US007223101B2

(12) United States Patent
Garrison et al.

(10) Patent No.: US 7,223,101 B2
(45) Date of Patent: May 29, 2007

(54) WEDGE FOR USE IN DENTAL RESTORATION

(76) Inventors: Tom Garrison, 18100 Lake Hills Dr., Spring Lake, MI (US) 49456; Robert Anderson, 11206 Garfield St., Coopersville, MI (US) 49404

( * ) Notice: Subject to any disclaimer, the term of this patent is extended or adjusted under 35 U.S.C. 154(b) by 390 days.

(21) Appl. No.: 10/608,203

(22) Filed: Jun. 27, 2003

(65) Prior Publication Data

US 2004/0014006 A1    Jan. 22, 2004

Related U.S. Application Data

(60) Provisional application No. 60/392,209, filed on Jun. 28, 2002.

(51) Int. Cl.
*A61C 7/00* (2006.01)
(52) U.S. Cl. ..................................... 433/149
(58) Field of Classification Search .............. 433/39, 433/148, 149
See application file for complete search history.

(56) References Cited

U.S. PATENT DOCUMENTS

| | | | | |
|---|---|---|---|---|
| 2,867,905 A | * | 1/1959 | Meacham | 433/149 |
| 2,891,313 A | * | 6/1959 | Crowley | 433/149 |
| 3,193,094 A | | 7/1965 | Schulstad | 206/63.5 |
| 3,473,226 A | * | 10/1969 | Arlers et al. | 433/149 |
| 3,510,948 A | * | 5/1970 | Walthall | 433/149 |
| 3,636,631 A | * | 1/1972 | Tofflemire | 433/149 |
| 3,815,243 A | | 6/1974 | Earnes | 32/63 |
| 3,890,714 A | | 6/1975 | Gores | 32/64 |
| 4,468,199 A | | 8/1984 | Weikel | 433/149 |
| 4,631,030 A | * | 12/1986 | von Weissenfluh | 433/149 |
| 5,527,181 A | * | 6/1996 | Rawls et al. | 433/149 |
| 5,890,900 A | * | 4/1999 | Fischer et al. | 433/149 |
| 5,890,901 A | * | 4/1999 | Fischer et al. | 433/149 |
| 6,074,210 A | | 6/2000 | Garrison | 433/149 |
| 6,402,514 B1 | | 6/2002 | Fischer et al. | 433/149 |
| 6,482,007 B2 | * | 11/2002 | Stanwich et al. | 433/149 |

* cited by examiner

*Primary Examiner*—Ralph A. Lewis
(74) *Attorney, Agent, or Firm*—Van Dyke, Gardner, Linn & Burkhart, LLP

(57) ABSTRACT

A dental wedge comprises an elongated body, which includes a distal end and a proximal end which tapers to the distal end. The distal end defines an insertion end and tilts upwardly. The elongate body has a first portion starting at the distal end and has a second portion that ends at the proximal end. The first portion has a generally triangular-shaped cross-section and the second portion has a generally trapezoidal cross-section.

29 Claims, 22 Drawing Sheets

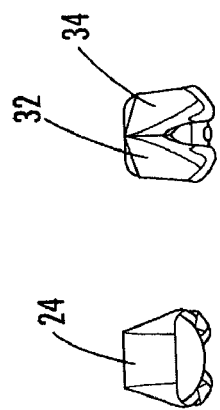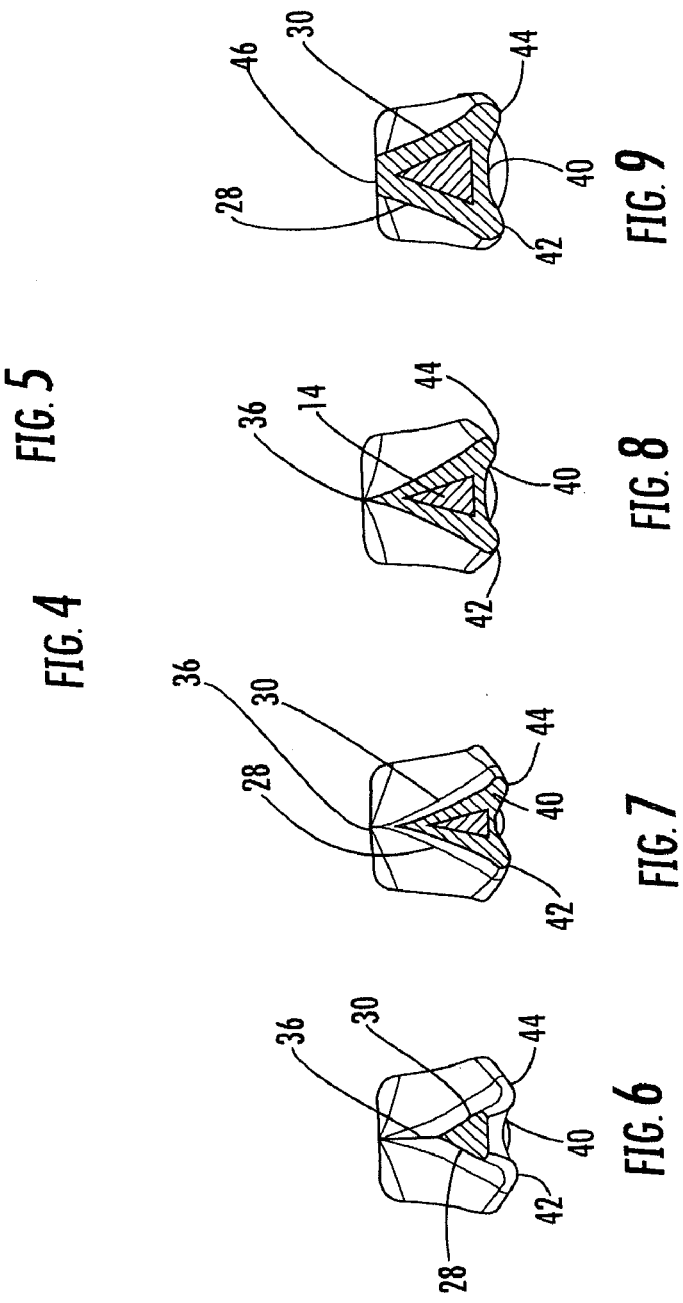

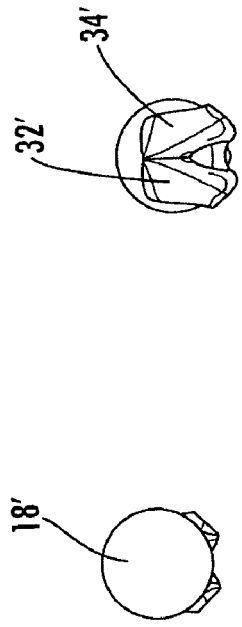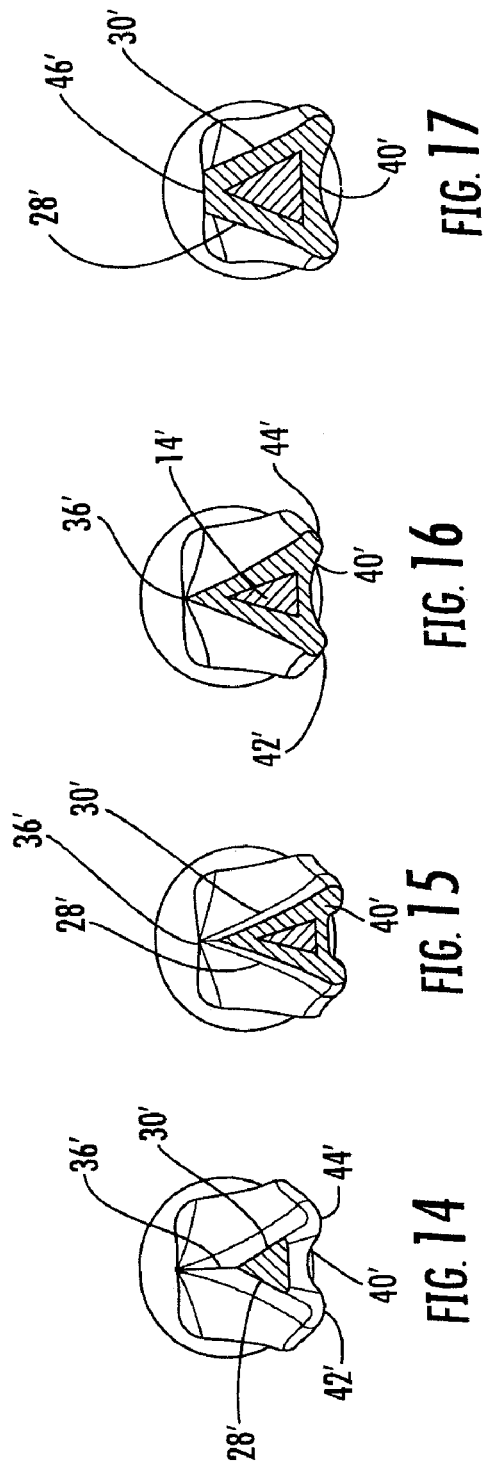

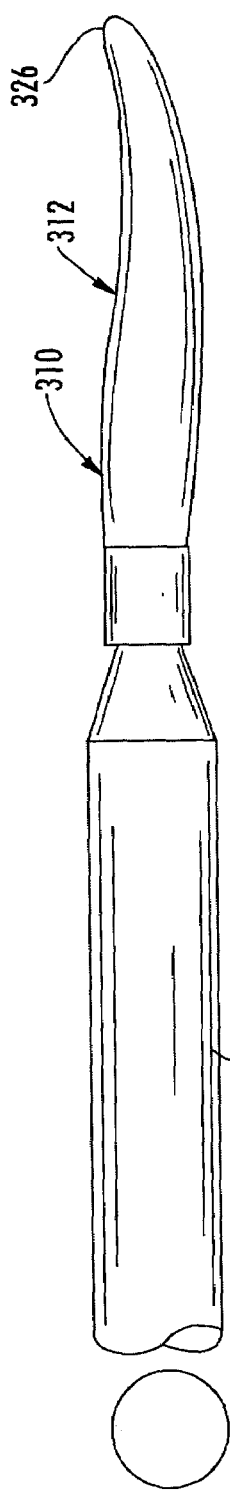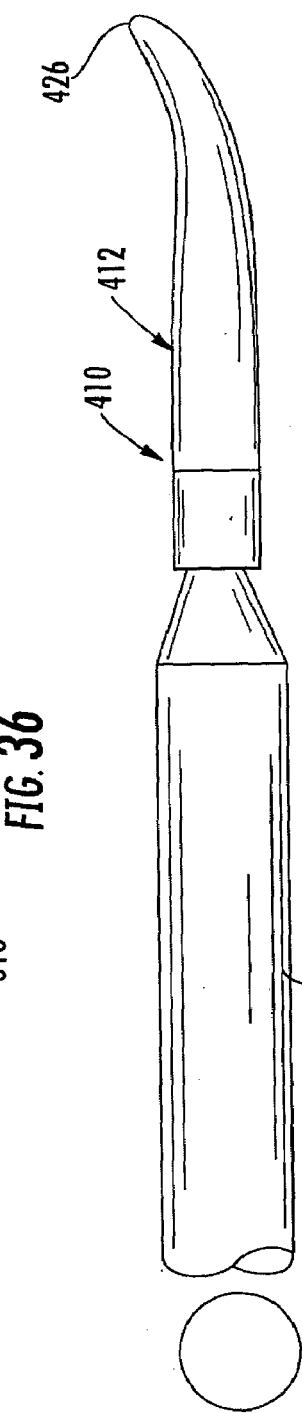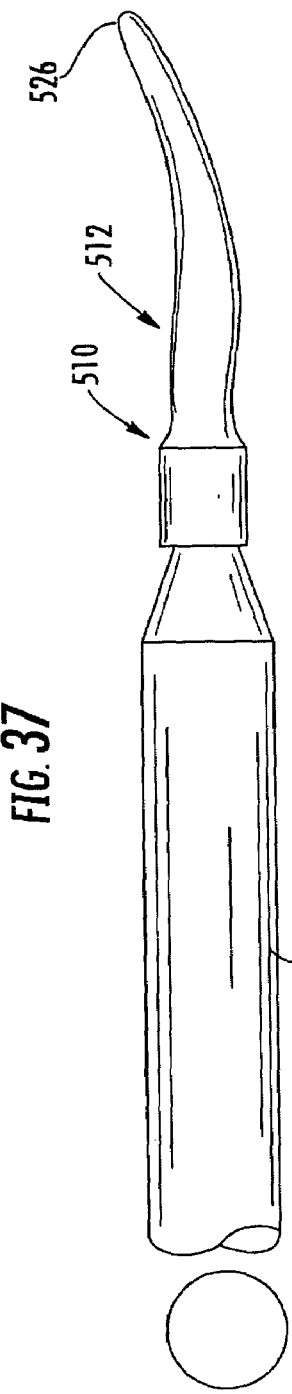

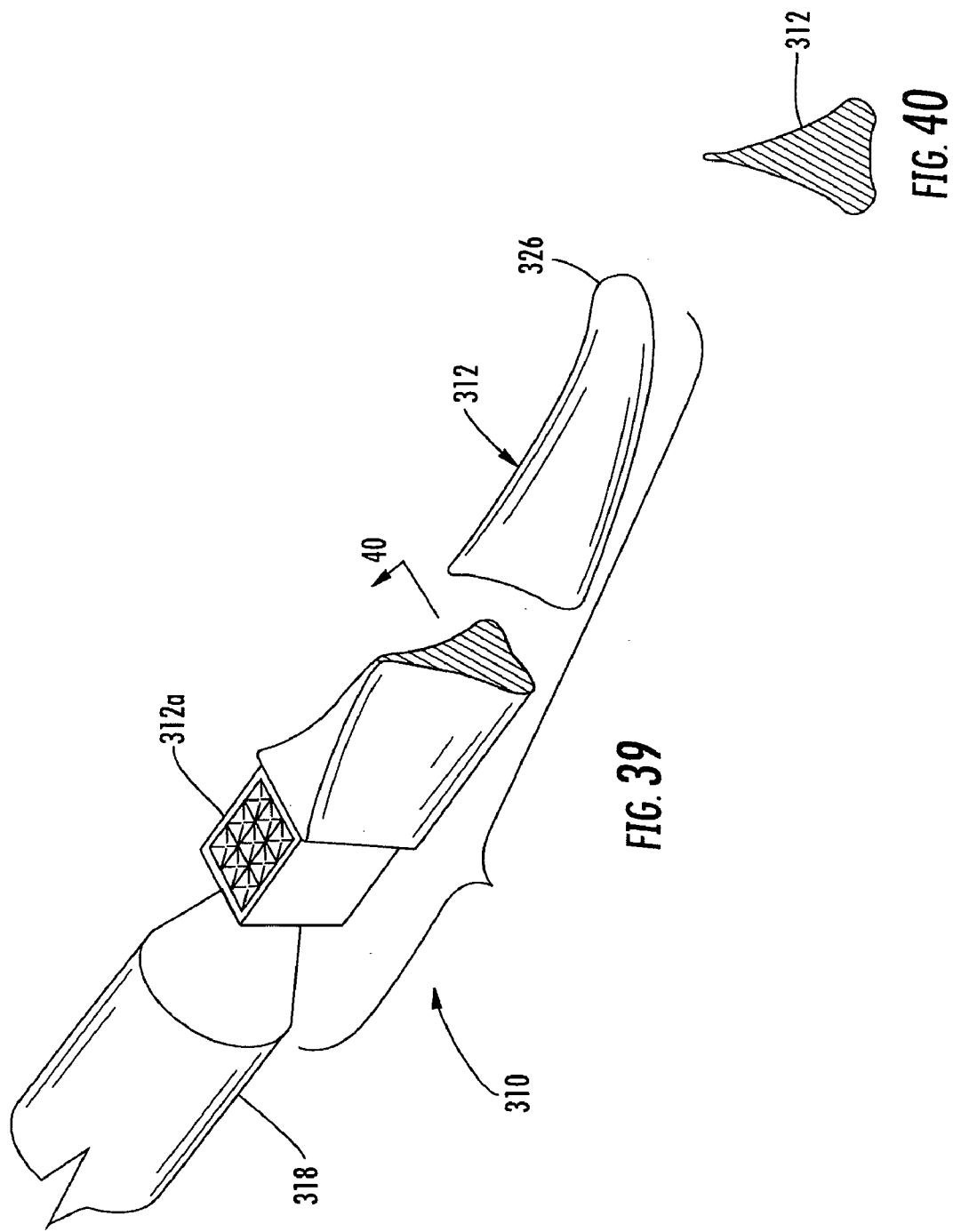

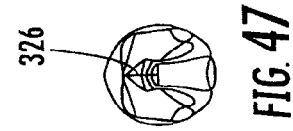
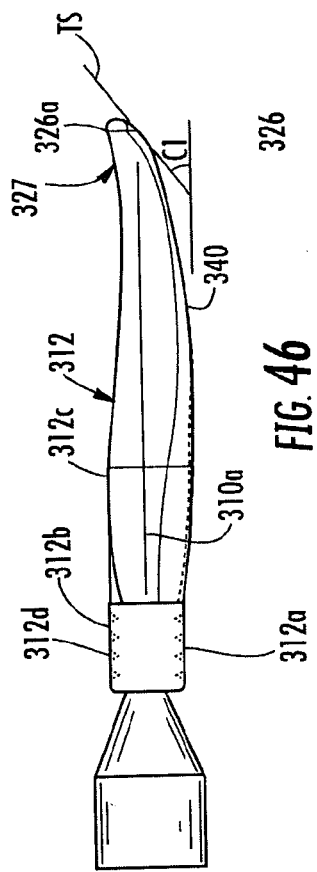
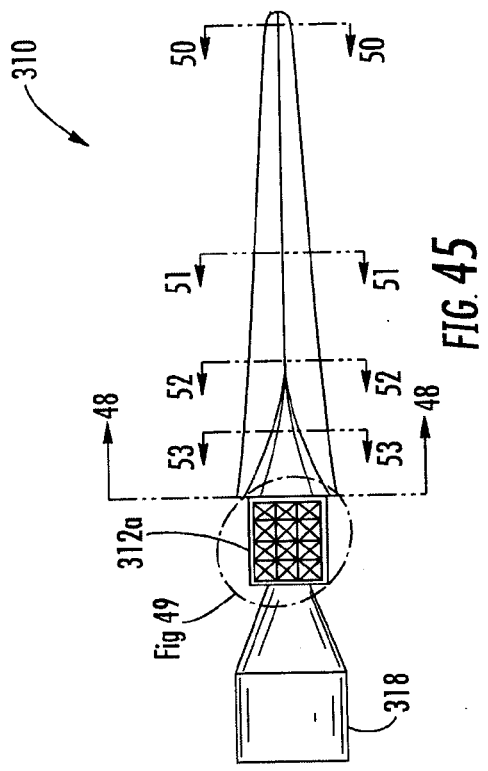
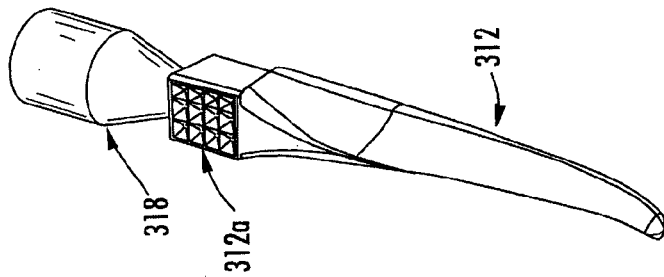

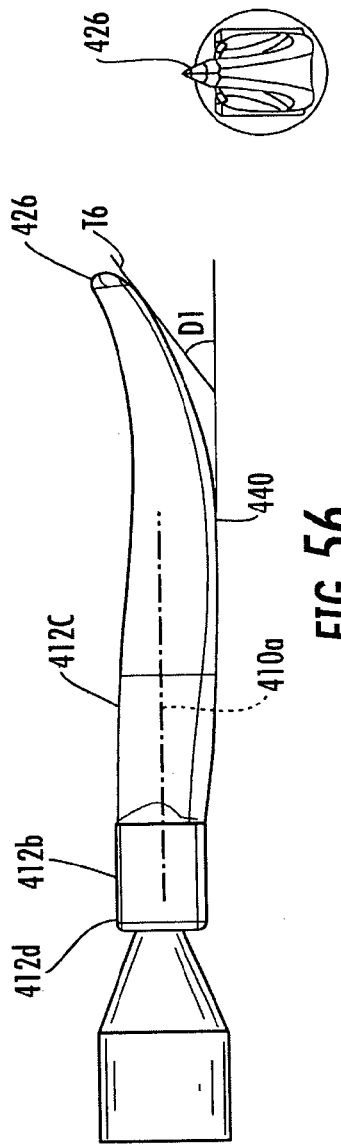
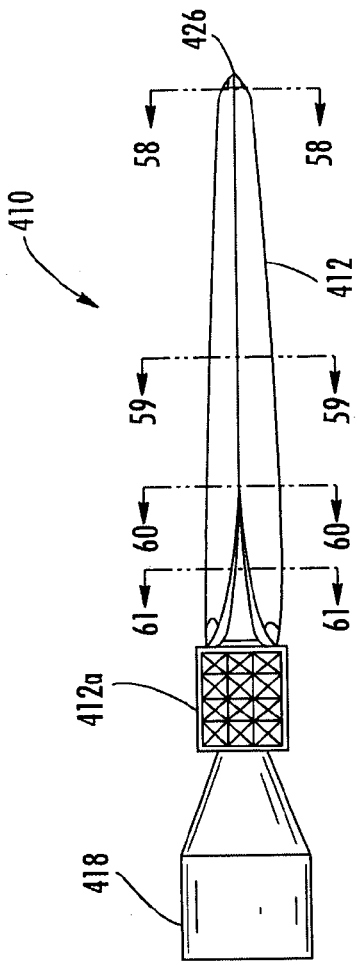
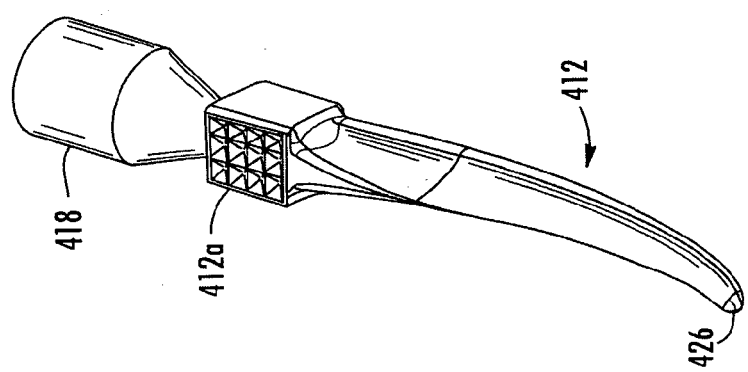

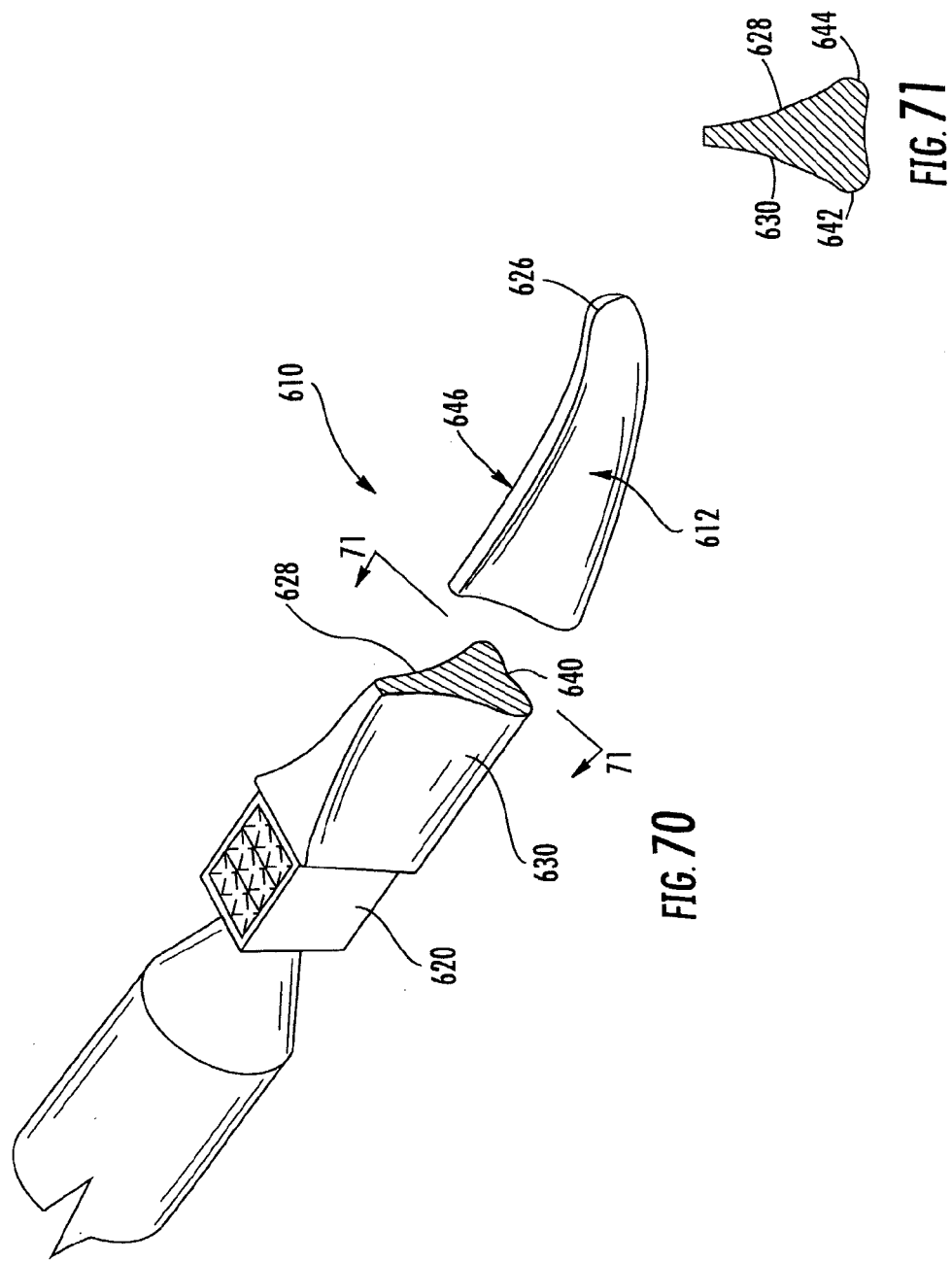

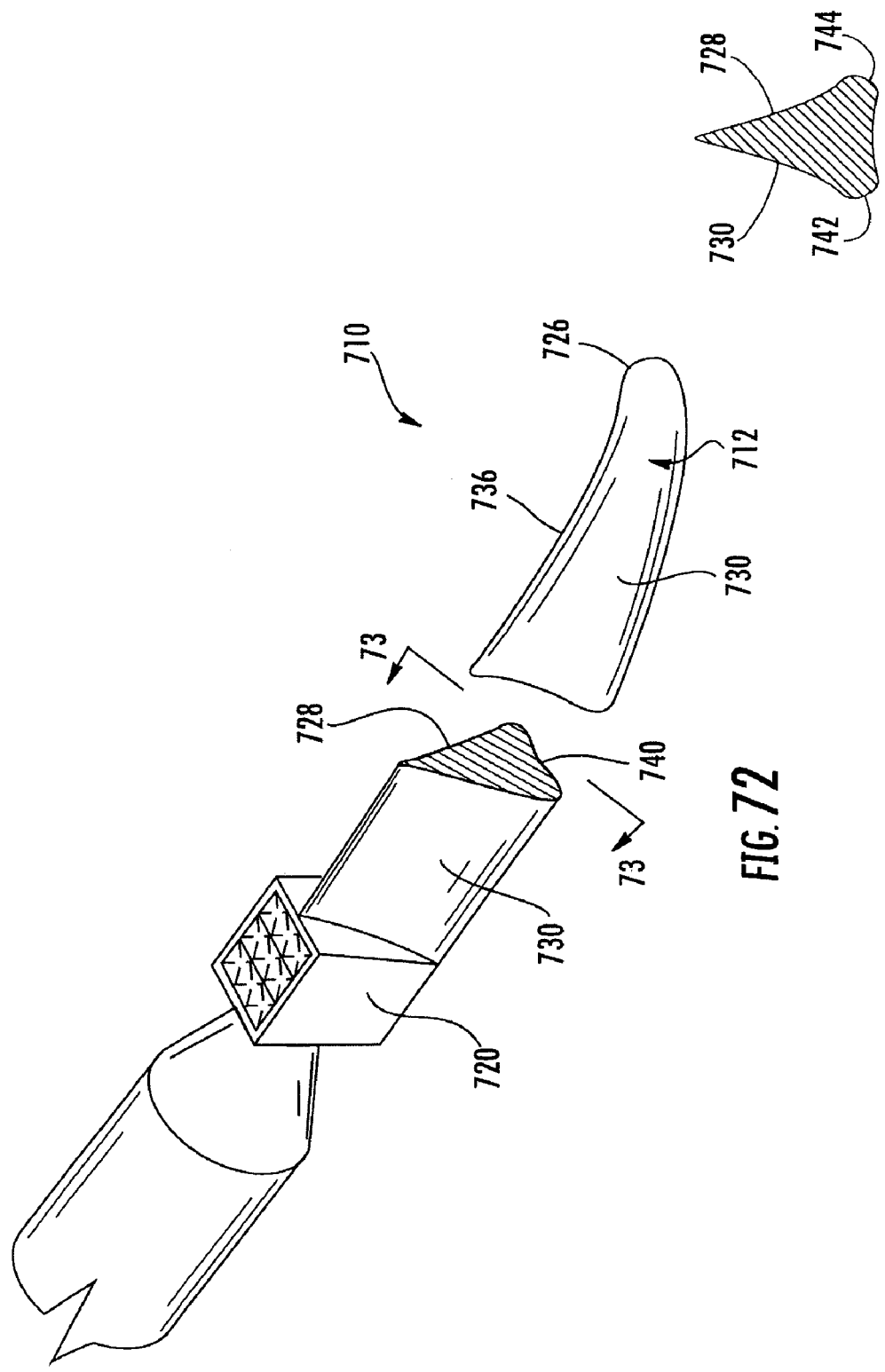

WEDGE FOR USE IN DENTAL RESTORATION

This application claims priority from pending U.S. provisional Pat. application entitled WEDGE FOR USE IN DENTAL RESTORATION, Ser. No. 60/392,209, filed Jun. 28, 2002, which is incorporated by reference in its entirety.

TECHNICAL FIELD AND BACKGROUND OF THE INVENTION

The present invention relates to a wedge and, more particularly, to a dental wedge used in dental restoration.

If a decayed portion of a tooth is located near its interproximal area, the tooth structure itself is usually insufficient to provide support to the filling material during the filling process. In order to retain the filling material in an excavated cavity, while the filling material hardens, a band is typically positioned about the tooth and secured tightly about the tooth so that the band forms an outer shell or matrix. In addition, it is often necessary to separate the adjacent teeth so that the filling material when hardened will provide adequate contact between the teeth to restore the teeth to their original state.

To separate teeth and, further, to hold the band in place, dentists often use a wedge typically formed from wood or plastic. The wedge is inserted in the interproximal area or space between the adjacent teeth at the gum line. When forced into the space, the wedge causes the teeth to separate and, further, seals the band against the tooth to thereby retain the filling material in the cavity and to prevent overhang of the filling material in the interproximal area.

Most commercially available wedges are tetrahedral in shape and tend to have relatively sharp edges, which can induce trauma to the gum tissue. Furthermore, some wedge designs have an abrupt cross sectional design where it starts out as a point and within a short distance it is at its maximum cross sectional area. Since wedges come in different sizes for different interproximal spaces the dentist has to pick out what size he/she thinks will work. When a dentist places a wedge in the interproximal space, which has an abrupt cross-sectional change, there is a likelihood that the wedge will back out. The reason for this is that when inserted between teeth, the wedge is subject to an equal but opposite force generated by the separated teeth. In some wedges, the sides of the wedges incorporate protuberances, such as ridges or ribs, such as disclosed in U.S. Pat. No. 3,815,243; U.S. Pat. No. 3,890,714; and U.S. Pat. No. 6,074,210, which are provided to reduce the backing out of the wedge from between the teeth. However, it has been found in some instances that these protuberances may leave the restored surface with an irregular surface, which may cause accumulation of plaque or food and, thus, lead to decay and periodontal problems.

In addition, the inserted distal end of a conventional wedge, which is pointed, can further induce damage to the gum tissue. Most wedges have an inherent design so that when placed or forced into the interproximal space they also have a tendency to shift horizontally or slightly downward due to the contact between the wedge and the teeth. This can induce bleeding, and if the wedge is forced thru the interproximal space (which it is normally), a pointed wedge could either be driven into or through the sulcus (the sulcus is the gum tissue that surrounds a tooth). This could result in the patient experiencing some discomfort, and could inhibit the dentist from performing a proper restoration.

Consequently, there is a need for an improved dental wedge, which permits placement of the wedge with minimal trauma to the gum tissue and, further, in a manner, which does not degrade the surface of the restoration when removed.

SUMMARY OF THE INVENTION

According to the present invention, a wedge for use in dental restoration is provided that reduces trauma to the gum tissue when inserted between adjacent teeth and, further, minimizes, if not eliminates, degradation of the surface of the restoration when removed.

In one form of the invention, a dental wedge includes an elongate body with a lower surface, a pair of spaced apart sides that extend from the lower surface, and a distal end. The body includes rounded corners at the juncture between the sides and the lower surface, and the distal end is also rounded such that the wedge does not present any sharp points or edges to the tissue when being inserted into the interproximal area between adjacent teeth to minimize trauma to the surrounding tissue.

Furthermore, the sides and the lower surface are concave to form a contoured body that provides increased contact between the wedge and the teeth and gum to increase friction between the wedge and the gum and teeth, which holds the wedge more securely in place and, further, provides more contoured contacts for the restoration. In one aspect, the corners at the juncture of the sides and the lower surface are radiused in a range of 0.003 inches to 0.050. In addition, the radii of the corners may vary across their respective lengths or may be generally uniform across their lengths.

In another form of the invention, a dental wedge includes an elongate body having a lower surface, a distal end, and a proximal end, which tapers to the distal end. The distal end defines an insertion end for insertion into the interproximal area between adjacent teeth. The insertion end is tilted upwardly relative to the lower surface of the elongate body wherein the distal end is engageable with at least one of the teeth when the wedge is inserted into the interproximal area between the adjacent teeth. The elongate body has a first portion starting at the distal end, which has a generally triangular-shaped cross-section, and a second portion, which ends at or adjacent the proximal end and which has a generally trapezoidal-shaped cross-section.

In one aspect, the distal end comprises an enlarged rounded distal end wherein the distal end of the wedge forms an abutment for engaging at least one of the teeth when the wedge is inserted into the interproximal area between the adjacent teeth. For example, the rounded distal end may comprise a generally spherical-shaped distal end.

In another aspect, the triangular-shaped cross-section and the trapezoidal-shaped cross-section define a base side and angled sides. The angled sides depend from the base side and form rounded corners with the base side to reduce trauma to the tissue when the wedge is inserted between the teeth. In a further aspect, the angled sides include concave portions.

According to yet another aspect, the elongate body has an outer surface which comprises a high friction material, such as an elastomer or rubber, including a thermoplastic elastomer, such as SANTOPRENE®, which reduces slippage of the wedge from between the adjacent teeth.

According to yet another form of the invention, a dental wedge includes an elongate body, which has a core and an exterior surface. The core extends along at least a portion of the longitudinal access of the elongate body and comprises a first material having a first hardness. The exterior surface is formed from a second material with a second hardness, which is less than the first hardness to form a generally soft exterior surface to reduce trauma to the tissue when the dental wedge is inserted between teeth and, further, so that the portion of the wedge between the teeth compresses resulting in enlarged portions on the inner and outer sides of the teeth which provide resistance to the wedge to slipping out from between the teeth. In addition, the exterior surface has a substantially uniform thickness across the length of the elongate body.

In one aspect, the core material comprises a substantially rigid material, such as plastic, including polypropylene or a polyethylene, for example, or a metal or wood. According to another aspect, the material of the exterior surface comprises an elastomer or rubber, including thermoplastic elastomer, such as SANTOPRENE®.

According to yet another form of the invention, the dental wedge of the present invention includes an elongate body that includes a base side and a pair of angled tapered sides, which are generally free of protuberances or indentations prior to insertion between the teeth. The angled tapered sides are joined with the base side and form rounded corners with the base side to minimize trauma to the tissue when the dental wedge is inserted between the teeth for dental restoration.

In yet another form of the invention, a dental wedge includes an elongate body that includes an exterior surface comprising a high friction material wherein the high friction material reduces slippage of the dental wedge when the dental wedge is inserted between teeth.

These and other objects, advantages, purposes, and features of the invention will become more apparent from the study of the following description taken in conjunction with the drawings.

DETAILED DESCRIPTION OF THE DRAWINGS

FIG. 1 is a perspective view of a dental wedge of the present invention;
FIG. 2 is a top plan view of the dental wedge of FIG. 1;
FIG. 3 is a side view of the dental wedge of FIG. 1;
FIG. 4 is an end view of the dental wedge of FIG. 3;
FIG. 5 is an end view of the distal end of the dental wedge of FIG. 3;
FIG. 6 is a cross-section view taken along line 6-6 of FIG. 2;
FIG. 7 is a cross-section view taken along line 7-7 of FIG. 2;
FIG. 8 is a cross-section view taken along line 8-8 of FIG. 2;
FIG. 9 is a cross-section view taken along line 9-9 of FIG. 2;
FIG. 10 is a perspective view of another embodiment of the dental wedge of the present invention;
FIG. 11 is a plan view of the dental wedge of FIG. 10;
FIG. 12 is a side elevation view of the dental wedge of FIG. 10;
FIG. 13A is an end view of the proximal end of the dental wedge of FIG. 12;
FIG. 13B is an end view of the distal end of the wedge of FIG. 11;
FIG. 14 is a cross-section view taken along line 14-14 of FIG. 11;
FIG. 15 is a cross-section view taken along line 15-15 of FIG. 11;
FIG. 16 is a cross-section view taken along line 16-16 of FIG. 11;
FIG. 17 is a cross-section view taken along line 17-17 of FIG. 11;
FIG. 18 is a perspective view taken of yet another embodiment of the wedge of the present invention;
FIG. 19 is a top plan view of the wedge of FIG. 18;
FIG. 20 is a side elevation view of the wedge of FIG. 19;
FIG. 21A is an end view of the proximal end of the wedge of FIG. 19;
FIG. 21B is an end view of the distal end of the wedge of FIG. 19;
FIG. 22 is a cross-section view taken along line 22-22 of FIG. 19;
FIG. 23 is a cross-section view taken along line 23-23 of FIG. 19;
FIG. 24 is a cross-section view taken along line 24-24 of FIG. 19;
FIG. 25 is a cross-section view taken along line 25-25 of FIG. 19;
FIG. 26 is a perspective view taken of a fourth embodiment of the wedge of the present invention;
FIG. 27 is a top plan view of the wedge of FIG. 26;
FIG. 28 is a side elevation view of the wedge of FIG. 27;
FIG. 29A is an end view of the proximal end of the wedge of FIG. 27;
FIG. 29B is an end view of the distal end of the wedge of FIG. 27;
FIG. 30 is a cross-section view taken along line 30-30 of FIG. 27;
FIG. 31 is a cross-section view taken along line 31-31 of FIG. 27;
FIG. 32 is a cross-section view taken along line 32-32 of FIG. 27;
FIG. 33 is a cross-section view taken along line 33-33 of FIG. 27;
FIG. 34 is an elevation view of the wedge of the present invention positioned between two teeth;
FIG. 35 is a plan view of the wedge and teeth of FIG. 34;
FIG. 36 is a side elevation view of a fifth embodiment of a wedge and its implement mounted on its insertion implement;
FIG. 37 is a side elevation view of a sixth embodiment of a dental implement and its insertion implement of the present invention;
FIG. 38 is a side elevation view of a seventh embodiment of the dental wedge and its insertion implement of the present invention;
FIG. 39 is a fragmentary perspective view of the dental implement of FIG. 36;
FIG. 40 is a cross-section view taken at line 40-40 of FIG. 39;
FIG. 41 illustrates the insertion of the dental wedge of the present invention between adjacent teeth for holding a band against the interproximal area of a tooth undergoing repair;
FIG. 42 illustrates the step of disconnecting the insertion implement from the wedge by the twisting of the insertion implement;
FIG. 43 illustrates the removal of the wedge from the insertion implement prior to placement between adjacent teeth;
FIG. 44 is a perspective view of the fifth embodiment of the dental wedge of the present invention;
FIG. 45 is a top plan view of the top plan view of the wedge of FIG. 44;
FIG. 46 is a side elevation view of the wedge of FIG. 45;
FIG. 47 is a distal end view of the wedge of FIG. 46;
FIG. 48 is a cross-section view taken along line 48-48 of FIG. 45;

FIG. 54 is a perspective view of the sixth embodiment of the dental wedge of the present invention;

FIG. 55 is a top plan view of the dental wedge of FIG. 54;

FIG. 56 is a side elevation view of the dental wedge of FIG. 53;

FIG. 57 is a distal end view of the dental wedge of FIG. 54;

FIG. 70 is a perspective view of the another embodiment of the dental wedge of the present invention;

FIG. 71 is a cross-section view taken along line 71-71 of FIG. 70;

FIG. 72 is a perspective view of the another embodiment of the dental wedge of the present invention; and FIG. 73 is a cross-section view taken along line 73-73 of FIG. 72.

DETAILED DESCRIPTION OF THE PREFERRED EMBODIMENTS

Referring to FIGS. 1–9, the numeral 10 generally designates a dental wedge of the present invention. As will be more fully described below, dental wedge 10 minimizes the trauma to the gum tissue when the dental wedge is inserted between teeth (as will be more fully discussed in reference to FIGS. 34 and 35) while providing a wedge that exhibits reduced slippage after insertion between the adjacent teeth.

Figure 1:
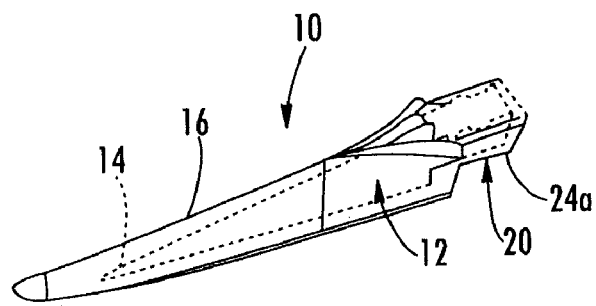
Figure 2:
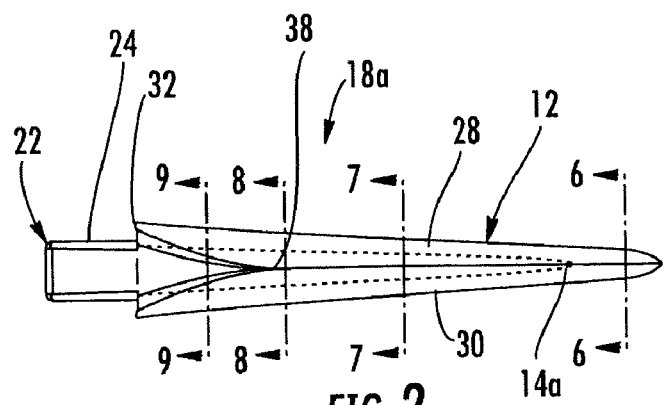
Figure 3:
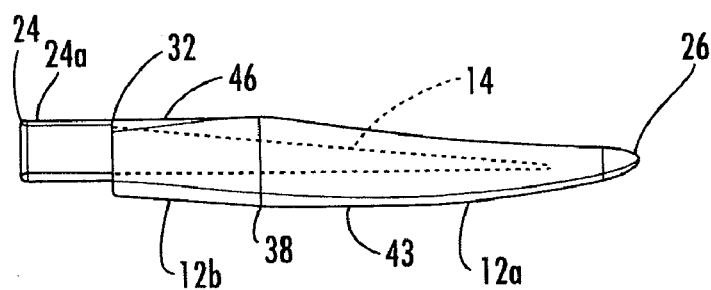

As best seen in FIGS. 1–3, dental wedge 10 includes an elongate body 12 that includes a core 14 and an outer surface 16. Preferably, outer surface 16 is softer than core 14 to minimize trauma to the gum tissue when wedge 10 is inserted in the interproximal area between adjacent teeth. For example, core 14 may comprise a plastic material, a metal or wood or other suitable generally rigid materials. In contrast, outer surface 16 is preferably formed from a softer plastic material, such as an elastomer, including a thermal plastic elastomer (TPE), such as SANTOPRENE®, having a hardness or durometer in a range of about 20 to 90 Shore A, more preferably, in a range of about 25 to 75 Shore A and, most preferably, in a range of about 30 to 60 Shore A.

In addition, outer surface 16 may be made from a material, which is generally compressible and, further, provides an increased or high friction surface so that when inserted between adjacent teeth, wedge 10 will withstand slipping back when placed in interproximal space between the adjacent teeth. In preferred form, when wedge 10 is inserted between adjacent teeth, the portion of the wedge between the adjacent teeth will compress so that the lingual (the inner side that faces the tongue) and buccal (the outer side facing the lips or cheek) portion of wedge 10 will be enlarged relative to the medial portion of the wedge to effectively lock the wedge in position between the adjacent teeth so that wedge 10 will resist slipping out between the adjacent teeth. Elongate body 12 is preferably formed by molding, such as injection molding, and, more preferably, by a two-shot molding process wherein the material forming outer surface 16 adheres to the material forming core 14 during the molding process. In addition, outer surface 16 preferably has a uniform thickness along the length of elongate body 12, with the distal end formed entirely from the outer surface material.

As best understood from FIGS. 1–3, wedge 10 is formed with a protuberance 22, which forms proximal portion 24, to provide a suitable end for engagement by a tool or suitable implement for removal of dental wedge 10. In the illustrated embodiment, protuberance 24 has a rectangular cross-section. It can be appreciated, however, that the shape and size of protuberance 24 may be varied as desired.

Referring to FIGS. 2 and 5–9, elongate body 12 includes sidewalls 28 and 30 that extend from distal end 26 to proximal end 32. As best seen in FIGS. 5–9, sidewalls 28 and 30 are generally free of protuberances or indentations and are angled and join at their upper corners to form a ridge or corner 36 that extends along elongate body 12 to an intermediate portion 38. In addition, side walls 28 and 30 are concave and, further, are tapered from proximal end 32 to distal end 26 so that the cross-section of elongate body 12 transitions from a generally triangular-shaped cross-section (shown in FIGS. 6–8) along a first portion 12a to a generally trapezoidal-shape cross-section (shown in FIG. 9), which extends along a second portion 12b. As understood from the illustrated embodiments, "triangular-shaped" "and "trapezoidal-shape" as used herein are used in its ordinary sense in they refer to three-sided and four-sided shape, but not necessarily to shapes with flat sides—in other words, the sides may be convex, curved or the like.

Figure 34:
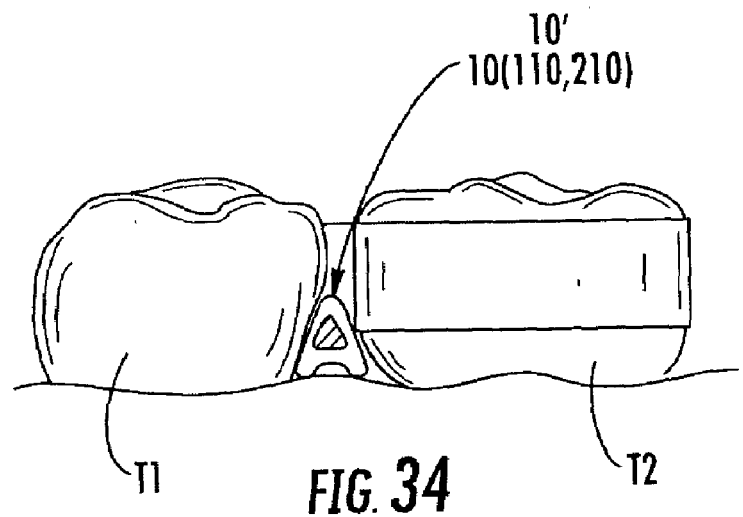
Figure 35:
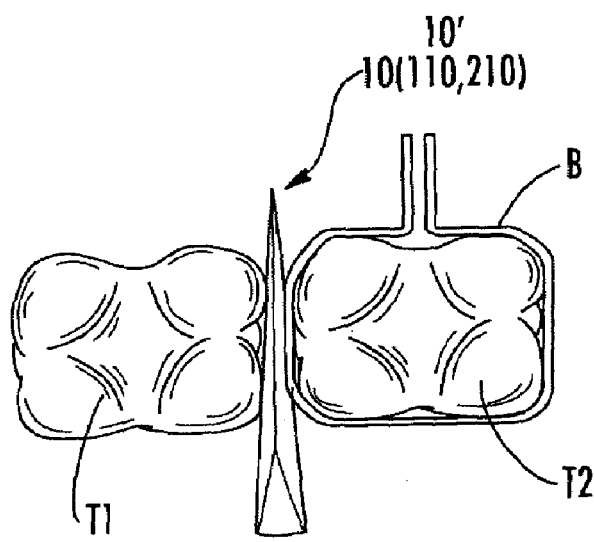

Sidewalls 28 and 30 extend upwardly from base side or base surface 40 and, further, preferably form rounded corners 42 and 44 at the juncture between sidewalls 28 and 30 and base side or surface 40. For example, corners 42 and 44 may have radii in a range of about 0.003 inches to 0.020 inches. Furthermore, corners 42 and 44 may have radii of curvature that are constant or vary along the length of wedge 10. In addition, base side 40 is preferably concave and may have a radius in a range of about 0.45 inches to 0.20 inches. In this manner, wedge 10 is free of any edges or sharp points so that when wedge 10 is inserted in the interproximal space between adjacent teeth (as shown in FIGS. 34 and 35), wedge 10 will induce minimal, if any, trauma to the gum tissue surrounding the teeth. Furthermore, given the wedge's smooth exterior surface, wedge 10 will not create any impressions on the restorative material.

Referring to FIGS. 2 and 9, when sidewalls 28 and 30 reach intermediate portion 38, the upper corners of sidewall 28 and 30 separate to form a planar upper surface 46. As a result, when wedge 10 is inserted in the interproximal portion of adjacent teeth, the transition between the triangular cross-section and the trapezoidal-shaped cross-section generates a separating force which separates the teeth. The two different cross-sectional shapes within the same wedge provide a gradual separating force and, further, produces an increased separating distance over the same path of travel of a triangular cross-sectioned wedge.

Referring to FIG. 3, distal end 26 comprises a generally rounded distal end and more preferably a duckbill-shaped distal end that has a sufficient roundness to minimize trauma to the gum tissue. In addition, distal end 26 is preferably sloped upwardly (relative to base surface or side 40) to further minimize the damage to the gum tissue when inserted into the interproximal area between the teeth. For example, distal end 26 is tilted upwardly from lowermost portion of corners 42, 44 of base side or surface 40 a distance in a range of about 0.020 inches to 0.10 inches and, more preferably, in a range of about 0.040 inches to 0.080 inches and, most preferably in a range of about 0.045 inches to 0.065 inches. Furthermore, upper corner 36 preferably tapers from intermediate portion 38 downwardly to distal end 26 with a slope in a range of about 0° to 18° and, more preferably, in a range of about 2° to 14° and, most preferably, in a range of about 4° to 10°. In this manner, as force is applied the gradual or incremental size change permits wedge 10 to gradually slide between the teeth and generates an improved separating force over the prior art devices while minimizing the trauma to the gum tissue surrounding the adjacent teeth. In addition, a second portion of elongate body 12 is similarly tilted upwardly relative to the lowermost surface of body 12, such as lowermost portion 43 of corners 42, 44, in a range of about 2° to 15°, more preferably, in a range of about 4° to 10°, which may ease the removal of dental wedge 10 from between the teeth.

As best seen in FIGS. 2 and 3, core 14 includes a terminal end 14a, which is spaced inwardly from distal end 26. It should be understood, however, that core 14 may extend to distal end 26. Referring to FIGS. 7–9, core 14 has a generally triangular-shaped cross-section from its terminal end 14a to proximal end 32 of elongate body 12, where the material forming core 14 transitions to a rectangular cross-section to form protuberance 24. Optionally, protuberance 24 may include a softer outer surface 24a formed from the same material forming exterior surface 16. In this manner, softer surface 24a provides an enhanced gripping surface for the tool or implement removing wedge 10.

Figure 10:
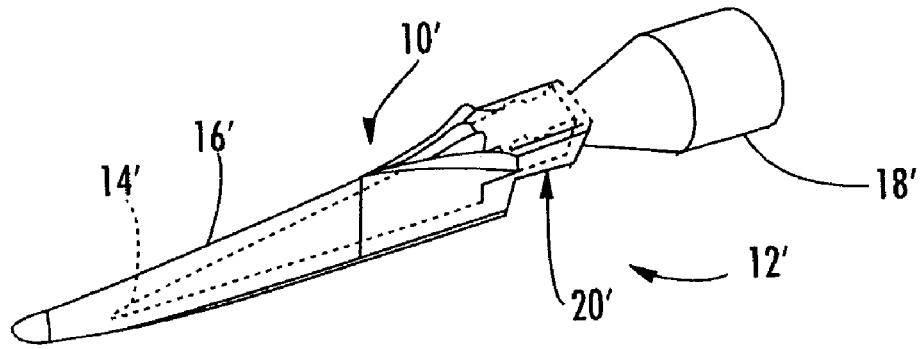
Figure 11:
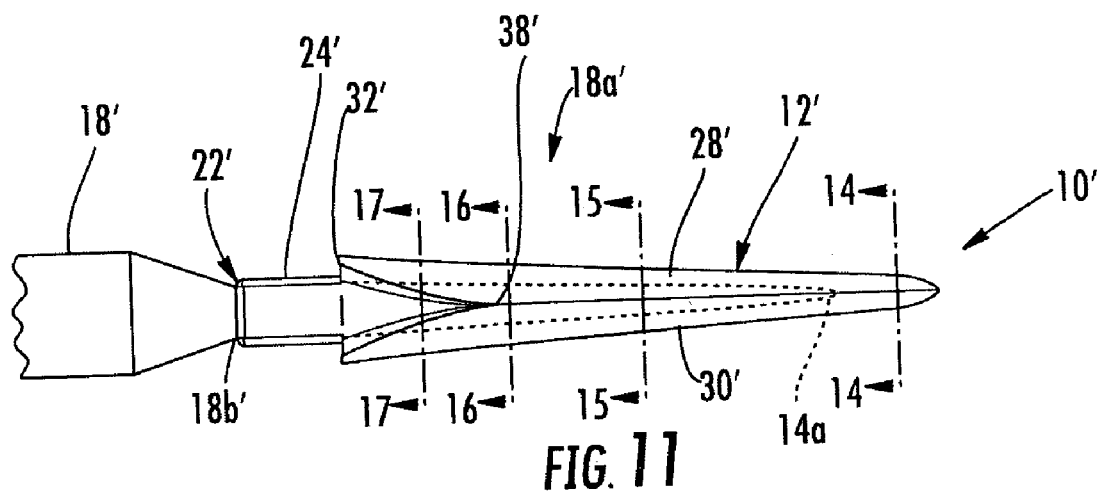
Figure 12:
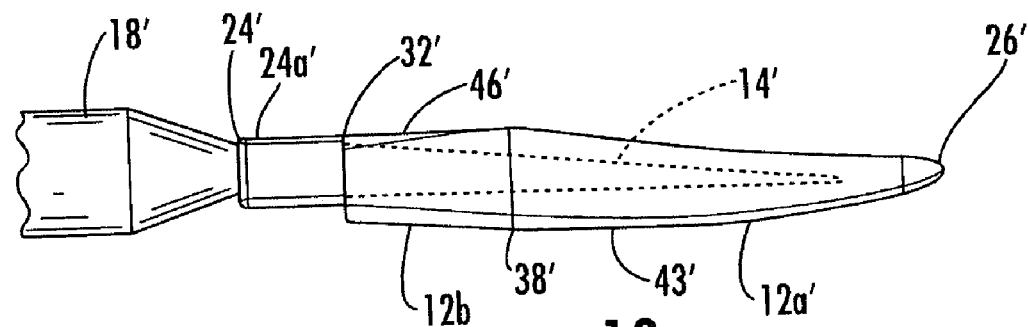

Referring to FIGS. 10–17, the numeral 10' generally designates another embodiment of the dental wedge of the present invention. As best seen in FIGS. 10–12, dental wedge 10' includes an elongate body 12', which includes a core 14' and an outer surface 16', similar to the pervious embodiment. Preferably, outer surface 16' is softer than core 14' to minimize trauma to the gum tissue when wedge 10' is inserted in the interproximal area between adjacent teeth. For examples of suitable materials, reference is made to wedge 10.

As best understood from FIGS. 10–12, wedge 10' is formed on the end of a stick 18', which comprises the material forming core 14'. Stick 18' includes a tapered neck 18b' so that when wedge 12' is placed between interproximal portion of adjacent teeth, wedge 12' may be broken off and separated from rod or stick 18' at reduced neck 18b' leaving protuberance 22', which forms proximal portion 24', which is suitable for engagement by a tool or suitable implement for removal of dental wedge 10'.

Referring to FIGS. 11 and 14–17, elongate body 12' includes sidewalls 28' and 30' which extend from distal end 26' to proximal end 32'. As best seen in FIGS. 14–17, sidewalls 28' and 30' are generally free of protuberances or indentations and are angled and join at their upper corners to form a ridge or corner 36' which extends along elongate body 12' to an intermediate portion 38'. In addition, side walls 28' and 30' are concave and, further, are tapered from proximal end 32' to distal end 26' so that the cross-section of elongate body 12' transitions from a generally triangular-shaped cross-section (shown in FIGS. 14–16) along a first portion 12a' to a generally trapezoidal-shape cross-section (shown in FIG. 17), which extends along a second portion 12b'. Sidewalls 28' and 30' extend upwardly from base side or base surface 40' and, further, preferably form rounded corners 42' and 44' at the juncture between sidewalls 28' and 30' and base side or surface 40'. For examples of suitable radii for corners 42' and 44' and for base side 40' reference is made to wedge 10.

Referring to FIGS. 11 and 17, when sidewalls 28' and 30' reach intermediate portion 38', the upper corners of sidewall 28' and 30' separate to form a planar upper surface 46'. As a result, when wedge 10' is inserted in the interproximal portion of adjacent teeth, the transition between the triangular cross-section and the trapezoidal-shaped cross-section generates a separating force which separates the teeth. The two different cross-sectional shapes within the same wedge provide a gradual separating force and, further, produces an increased separating distance over the same path of travel of a triangular cross-sectioned wedge.

Referring to FIG. 12, distal end 26' comprises a generally rounded distal end that has a sufficient roundness to minimize trauma to the gum tissue. In addition, distal end 26' is preferably sloped upwardly (relative to lower most surface 43' of corners 42', 44' or side 40') to further minimize the damage to the gum tissue when inserted into the interproximal area between the teeth. Again, reference is made to wedge 10 for examples of angles or slopes and distances of the tilt of distal end 26' and of second portion 12b' of wedge 10'.

As best seen in FIGS. 11 and 12, core 14' includes a terminal end 14a', which is spaced inwardly from distal end 26'. It should be understood, however, that core 14' may extend to distal end 26'. Referring to FIGS. 15–17, core 14' has a generally triangular-shaped cross-section from its terminal end 14a' to proximal end 32' of elongate body 12', where the material forming core 14' transitions to a rectangular cross-section to form protuberance 24'. Optionally, protuberance 24' may include a softer outer surface 24a' formed from the same material forming exterior surface 16'. In this manner, softer surface 24a' provides an enhanced gripping surface for the tool or implement removing wedge 10'.

Figure 18:
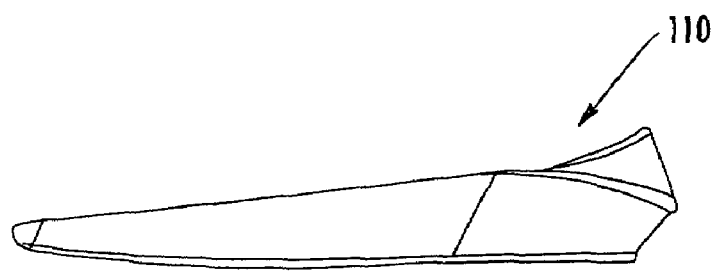
Figure 19:
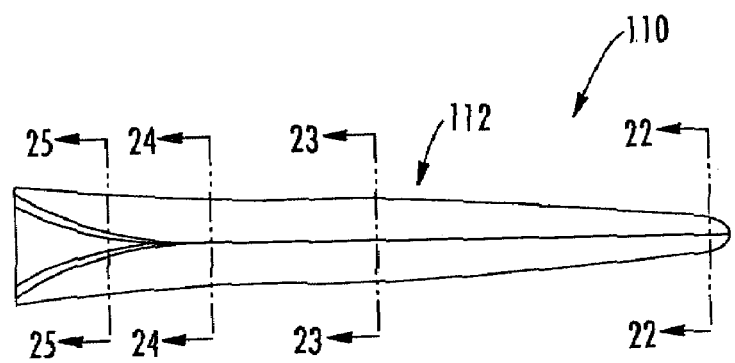
Figure 20:
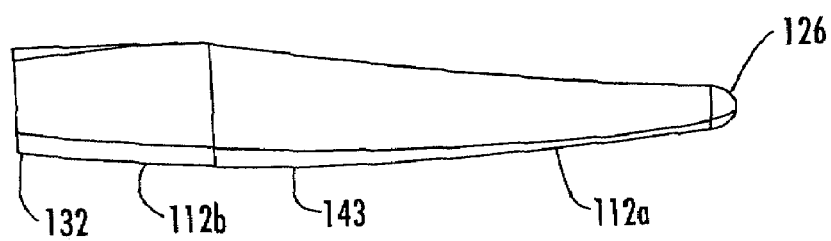
Figure 21A:
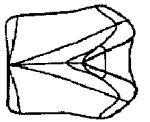
Figure 21B:
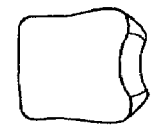

Referring to FIG. 18, the numeral 110 generally designates another embodiment of the dental wedge of the present invention. Dental wedge 110 is of similar construction to dental wedge 10 and includes an elongate body 112, which is formed from a uniform material, such as plastic, including polypropylene, a metal or wood or other suitable materials, having a durometer in a range of about 20 to 90 Shore A, more preferably, a durometer in a range of about 25 to 75 Shore A and, most preferably, in a range of about 30 to 60 Shore A. As used herein, the term "uniform material" is intended to mean that the material is substantially the same across the cross-section of the body through the material may be made of several components.

As best seen in FIGS. 22–25, elongate body 112 has a generally solid cross-section which transitions between a generally triangular cross-section over a first portion 112a of elongate body 112 to a generally trapezoidal cross-section over a second portion 112b of elongate body 112, similar to the previous embodiment.

Figure 25:
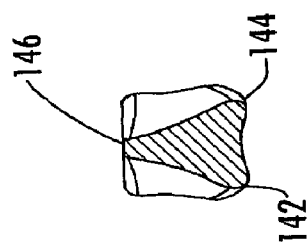
Figure 24:
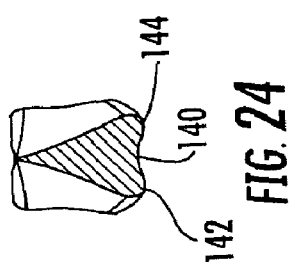
Figure 23:
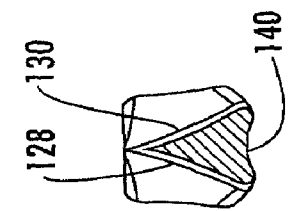

Referring to FIGS. 23–25, similar to the previous embodiment, elongate body 112 includes angles sides 128 and 130 which are generally concave and which extend from distal end 126 to proximal end 132. Sidewalls 128 and 130 join at their upper corners to form upper edge 136 of elongate body 112 but diverge to form generally planar upper surface 146 over the second portion of elongate body 112 to thereby form the trapezoidal-shaped cross section. Similar to the previous embodiments, sides 128 and 130 extend from lower surface 140 with each side including radiused corners 142 and 144 at the juncture with the lower surface 140.

In the illustrated embodiment, distal end 126 includes a rounded distal end having a larger radius than distal end 26 of wedge 10, for example. Distal end 126 similarly tilts upwardly relative to the lower most surface 143 of corners 142 and 144. Reference is made to the previous embodiment for examples of suitable angular ranges for the degree of upward tilt for distal end 126. In addition, base surface or side 140 is also similarly concave but with a larger radius than surface 40, for example, in a range of about 0.020 inches to 0.060 inches and, more preferably, in a range of about 0.025 inches to 0.55 inches and, most preferably, in a range of about 0.030 inches to 0.50 inches.

Figure 22:
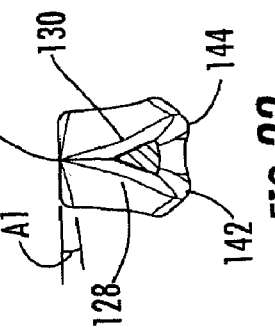
Figure 26:
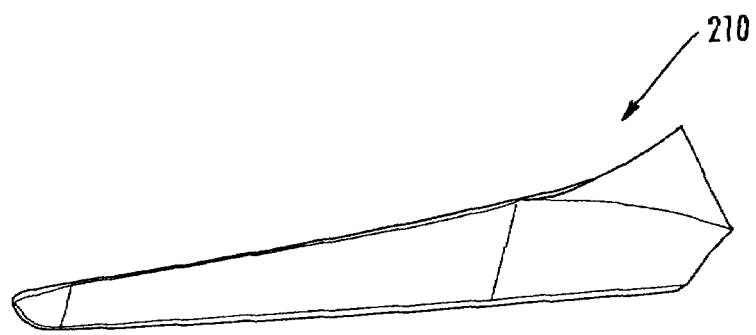
Figure 27:
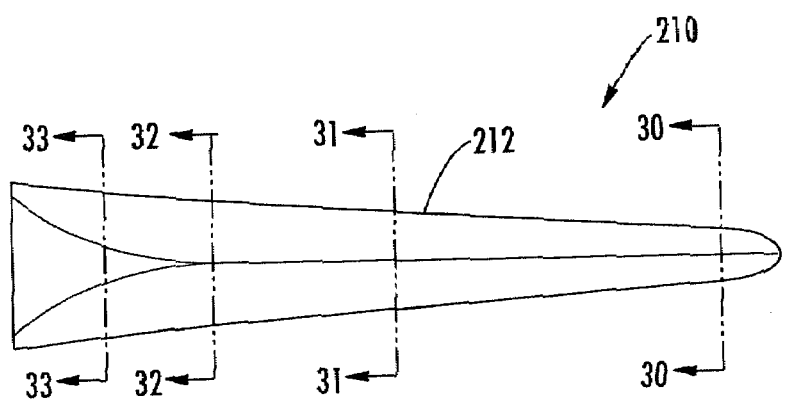
Figure 28:
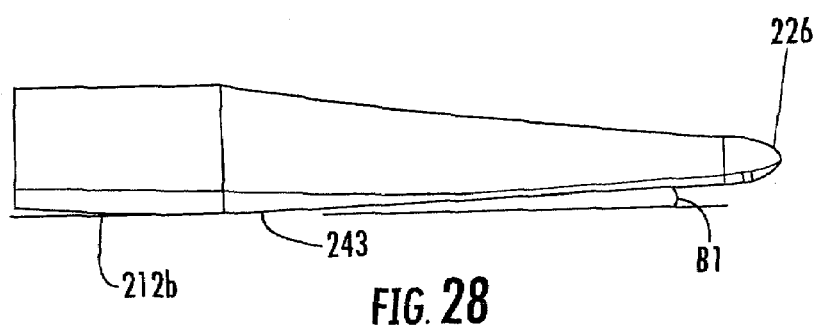
Figure 33:
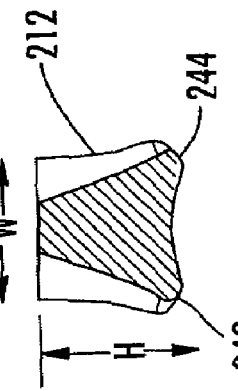
Figure 29B:
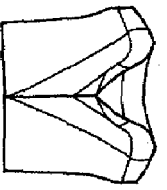
Figure 32:
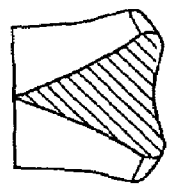
Figure 29A:
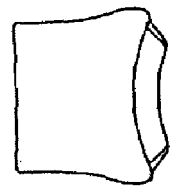
Figure 31:
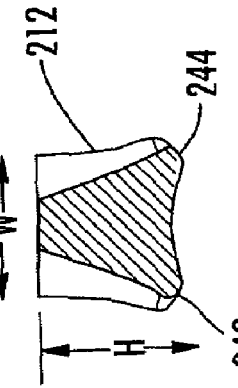
Figure 30:
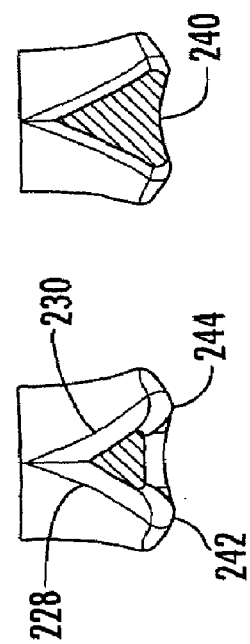

As best seen in FIGS. 22 and 23, the upper corners of sidewalls 128 and 130 along second portion 112b are preferably angled at an angle A1 in a range of about 1° to 10° and, more preferably, in a range of about 2° to 6°.

Referring to FIGS. 26–33, the numeral 210 generally designates another embodiment of the present invention. Dental wedge 210 is of similar construction to dental wedge 110 and includes an elongate body 212, which is formed from a uniform material, such as plastic, and includes generally a solid cross-section as seen in FIGS. 30–33. In the illustrated embodiment, second portion 212b of elongate body 212 is similarly tilted upwardly relative to the lower most surface 243 of corners 242, 244 or base side 240 or body 212 and angled at an angle B1 in a range of about 1° to 10° and, more preferably in a range of about 2° to 6°. Distal end 226 of elongate body 212 has a smaller radiused distal end and, farther, is angled in a range of about 0° to 18°, more preferably, in a range of about 2° to 14° and, most preferably in a range of about 4° to 10° from lowermost surface 243 of base side 240. In addition, elongate body 212 has a greater width dimension than elongate body 112 and has a second portion 212b with width and height dimensions W and H, which are approximately equal, similar to second portion 12b of elongate body 12. Furthermore, the upper corners of sidewalls 228 and 230 along second portion 212b are generally parallel.

Referring to FIGS. 34 and 35, wedges 10, 10', 110, or 210 are placed between adjacent teeth T1 and T2, with their distal ends (26, 26', 126, or 226) inserted first. In reference to the second embodiment, stick 18' is used to urge wedge 10' between the adjacent teeth. Using pressure from stick 18', wedge 10' is urged between teeth T1 and T2 to provide adequate separation force between teeth T1 and T2 until a resistance is detected. In most restorative dental work, a band B is placed at least partially around a tooth under construction, such as tooth T2. It can be appreciated that a band that encircles the tooth may also be used (shown in phantom in FIGS. 34 and 35). Typically, band B is placed around the tooth with the wedge 10 (110 or 210) inserted to separate the teeth and conform and hold the band B against the tooth to be restored. To remove the wedge from between the teeth, a dental implement simply grasps the proximal end, or in the case of wedges 10 or 10' the protuberance, so that the wedge can be pulled from between the teeth.

Typical length dimensions of the dental wedges of the present invention range from about 0.5 inches to 0.75 inches and, further, have a sloped distal end that is angled in a range of about 3° to 10°, more preferably, in a range of about 5° to 8° and, most preferably, in a range of 5.5° to 7°. Furthermore, the width of the dental wedges of the present invention typically ranges from approximately 0.05 inches to 0.15 inches and, more preferably, in a range of 0.06 inches to 0.12 inches, for example. In addition, the overall height of the wedges typically ranges from approximately 0.075 inches to 0.15 inches, for example.

Referring to FIGS. 37–39, numerals 310, 410, and 510 generally designate fifth, sixth, and seventh embodiments, respectively, of the wedge of the present invention. Wedges 310, 410, and 510 are of generally similar construction to wedges 110 and 210 and are formed from a uniform material, such as plastic, and include a generally solid cross-section, as will be more fully described below. However, it can be appreciated that wedges 310, 410, and 510 may comprise composite wedges similar to wedge 10. As best seen in FIGS. 36–68, wedges 310, 410, and 510 similarly incorporate wedge-shaped elongate bodies that transition from a trapezoidal-shaped cross-section to a triangular-shape cross-section to provide an increased separation force over conventional wedges and, further, incorporate curved lower surfaces and curved corners to minimize trauma to the tissue when the respective wedge is inserted between adjacent teeth.

In addition, to varying degrees each wedge incorporates an upwardly turned distal end to facilitate insertion and, again, to reduce tissue trauma. In the illustrated embodiments, wedges 310, 410, and 510 incorporate varying degrees of tilt or uplift in their distal ends 326, 426, and 526 and, further, illustrate various sizes of wedges with modified cross-sections that vary across their respective lengths to vary the separation force generated by the insertion of the respective wedges, for example, and further vary the degree or rate of transition from the triangular shaped cross-section to the trapezoidal-shaped cross-section to reduce the trauma.

Furthermore, the respective distal ends 326, 426, and 526 comprise rounded or bulbous distal ends to reduce trauma to the gum tissue, namely the sulcus and/or papilla when inserted between adjacent teeth. In addition, as noted above, distal ends 326, 426, and 526 are preferably sloped upwardly (relative to their base surfaces or their lower sides) to further minimize the damage to the gum tissue when inserted into the interproximal area between the teeth and, as will be more fully described, to enhance the retention of the wedge between the adjacent teeth. For example, distal ends 326, 426, and 526 are tilted upwardly from lowermost portion of their respective base surfaces a distance in a range of about 0.040 inches to 0.25 inches and, more preferably, in a range of about 0.050 inches to 0.225 inches and, most preferably in a range of about 0.06 inches to 0.20 inches. From the foregoing descriptions, it will be appreciated that the upturned distal ends of the wedges are sufficiently upturned to catch on the backside of the teeth to limit the axial movement of wedge 510 between the adjacent teeth. The axial movement is then further limited by the increased surface contact provided between the wedges and the adjacent teeth and gum tissue to provide a wedge that exhibits improved retention between the adjacent teeth.

Figure 41:
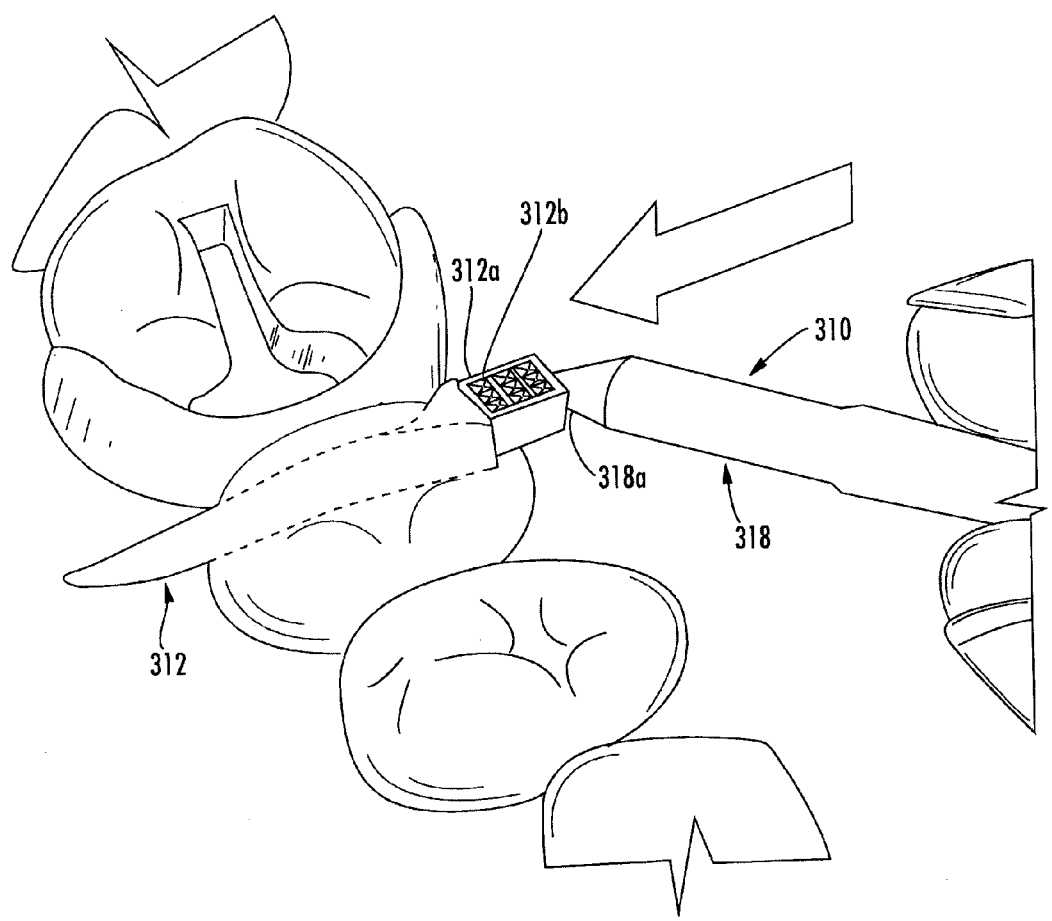
Figure 42:
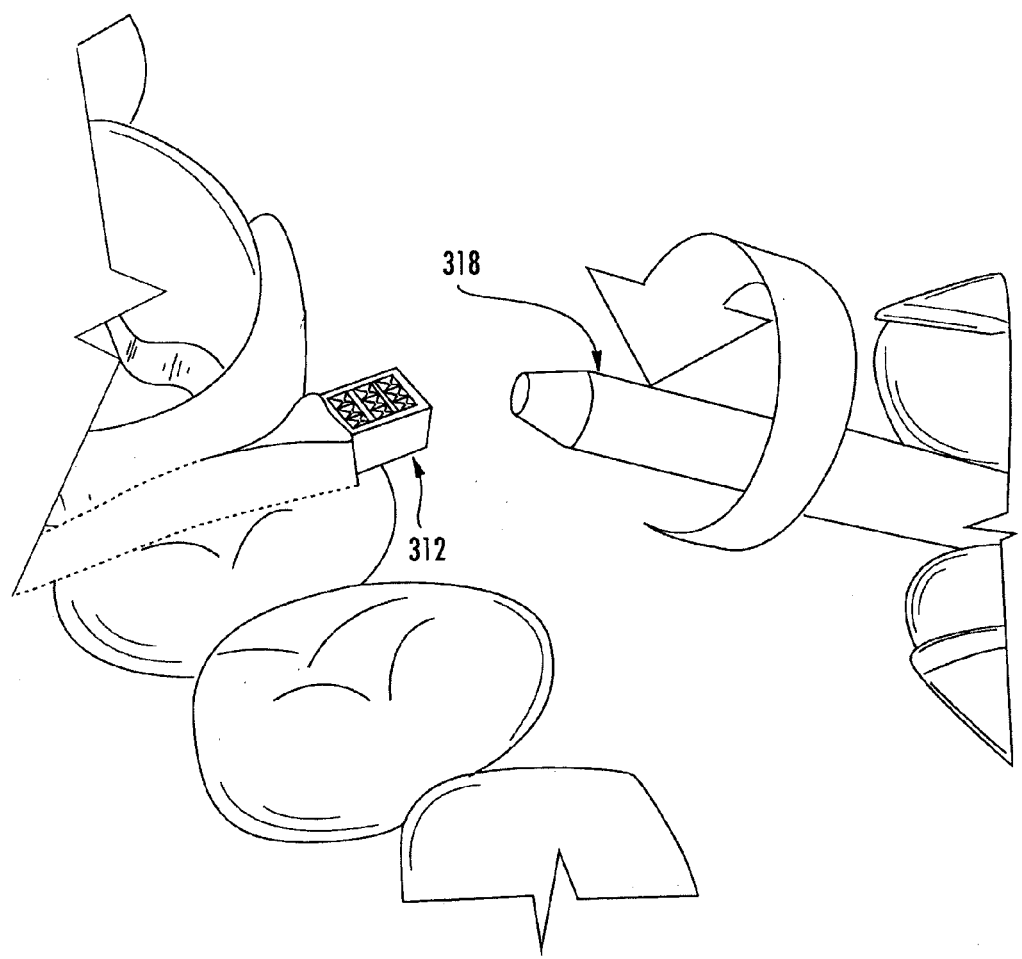

Referring to FIG. 41, for ease of reference, reference will be made to wedge 310 for a general description of the overall structure of the wedge and, further, for the method of insertion and removal of the wedge by its insertion implement 318. As noted above, wedge 310 is formed from a generally uniform material and includes an elongate body 312. Proximal end portion 312a of body 312 includes a generally rectangular cross-section and, further, incorporates a gripping surface 312b to facilitate removal of the wedge once the wedge is placed between adjacent teeth. In the illustrated embodiment, gripping surface 312b comprises a plurality of indentations, such as diamond-shaped indents or recesses. As will be more fully described below, elongate body 312 has a cross-section that transitions from a generally trapezoidal shape adjacent proximal end portion 312a to a substantially triangular-shaped cross-section through its medial portion to its distal end 326. In addition, distal end portion 327 is tilted upward relative to the lower surface 340 of elongate body and is angled such that the tangent line T5 forms an angle C1 with respect to base 340 in a range of about 20° to 50° and, more preferably, in a range of about 22° to 44°. In addition, distal end 326 is tilted upwardly with respect to the central longitudinal axis 310a of wedge 310 such that its upper surface 326a is generally aligned with the upper surface 312b of elongate body 312 and, further, generally aligned with the upper surface 312d of proximate end portion 312a.

As previously noted, referring to FIGS. 49–53, the cross-section of wedge 310 varies across its longitudinal axis 310a with proximal end portion 312a having a generally square- or rectangular-shaped cross-section (FIG. 49), which provides the gripping surface for wedge 310. Adjacent proximal end portion 312a, elongate body 312 has a wedge-shaped portion with a general trapezoidal-shaped cross-section initially having an upper side 346 that is slightly smaller in width than the lower side 340. To reduce trauma to the gum tissue surrounding the teeth, rounded lower corners 340a and 340b have radii of curvature in a range of about 0.010 inches to 0.050 inches and, more preferably, in a range of about 0.02 inches to 0.040 inches and, most preferably, in a range of about 0.026 inches to 0.030 inches. Further, elongate body 312 includes rounded upper corners 346a and 346b that have radii of curvature in a range of about 0.18 inches to 0.22 inches.

Figure 51:
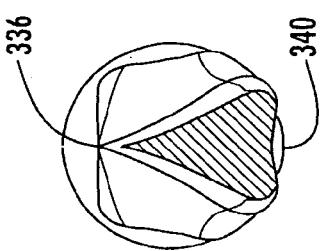
FIG. 51 is a cross-section view taken along line 51-51 of FIG. 45.

As best understood from FIG. 51, upper side 346 reduces in width such that the cross-section of body 312 transforms from a trapezoidal-shaped cross-section to a triangular-shaped cross-section as shown in FIG. 51. In addition, the radii of curvature of the opposed corners of upper side 346 reduce until the cross-section of the body transitions to a triangular shape where the corners converge to form an upper ridge or edge 336. Corners 340a and 340b of lower side 340 similarly reduce in curvature but maintain a radii of curvature of decreasing magnitude as the cross-section approaches distal end 326 of elongate body 312, where the cross-section of body 312 then increases again to form the rounded or generally spherical shaped distal end 326.

Figure 49:
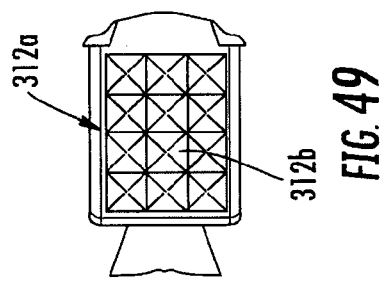
FIG. 49 is an enlarged plan view of detail 49-49 of FIG. 45.
Figure 52:
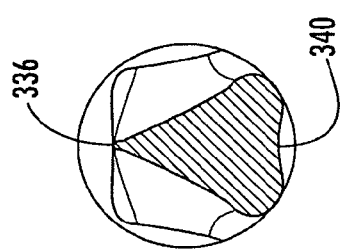
FIG. 52 is a cross-section view taken along line 52-52 of FIG. 45.
Figure 48:
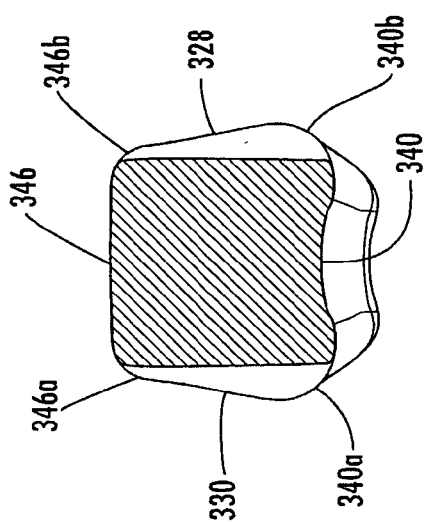

As best seen in FIG. 46, medial portion 312c of elongate body 312 includes a slightly curved lower surface that provides an extended contact area, with distal end 326 tilting upwardly with respect to the medial portion and with the proximal portion 312d also raised above lower surface 340. In addition, as best seen in FIG. 49, body 312 has an enlarged interface with proximal portion 312a such that the opposed sides 328 and 330 of elongate body 312 extend or project outwardly relative to proximal portion 312a. In addition, as viewed in FIG. 45, sides 328 and 330 have a generally linear taper from the interface with proximal end 312a to distal end 326. Similar to the previous embodiments, lower side 340 has a reverse curve curvature with a radius of curvature that varies in a range of about 0.070 to 0.130 inches and, more preferably, in a range of about 0.080 to 0.11 inches.

Figure 43:
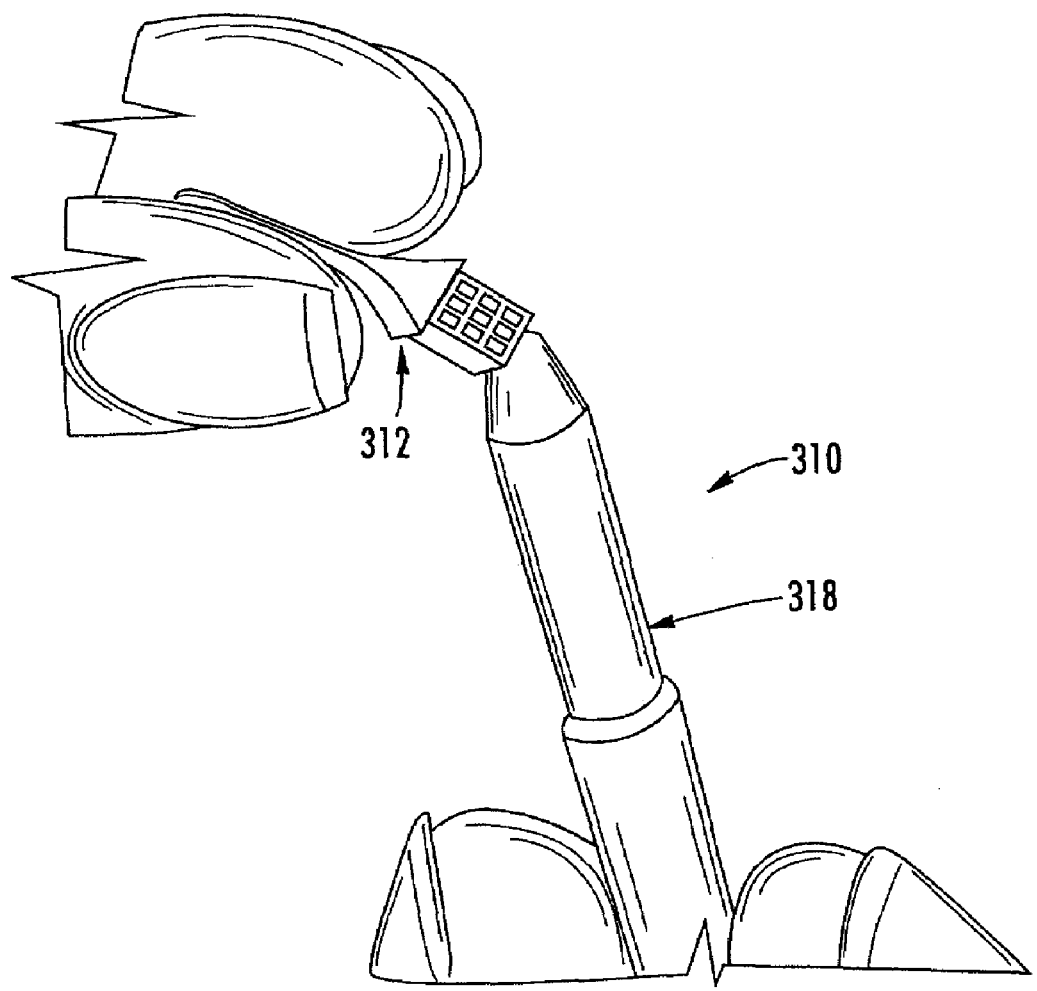
Figure 50:
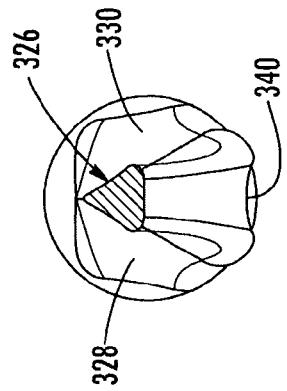
FIG. 50 is a cross-section view taken along line 50-50 of FIG. 45.
Figure 53:
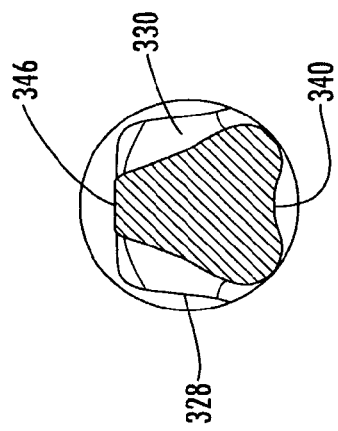
FIG. 53 is a cross-section view taken along line 53-53 of FIG. 45.

Referring again to FIGS. 42 and 43, wedge 310 is urged into position between adjacent teeth by insertion implement 318. Similar to the previous embodiment, wedge 310 is molded and formed on the end of a rod-shaped insertion implement 318 and includes a neck with a reduced diameter 318a, which permits the insertion implement 318 to be broken off the wedge once the wedge is placed between the teeth. For example, as best illustrated in FIG. 43, insertion implement 318 may be rotated or twisted relative to wedge 310 to break-off implement 318 from wedge 310. Alternately, as shown in FIG. 44, implement 318 may be disconnected from wedge 310 prior to insertion into the teeth.

Referring to FIGS. 37 and 54–61, dental wedge 410 similarly includes an elongate body 412 with an upwardly turned distal end 426 and slightly raised proximal end portion 412a that provides a gripping surface, and which has a rectangular cross-section similar to the previous embodiment. Referring to FIG. 56, distal end 426 is similarly tapered upwardly and, further, extends above proximal end portion 412a and above the upper surface of insertion implement 418. For example, distal end 426 may extend above insertion implement 418 a distance in a range of about 0.005 to 0.050 inches and, more preferably in a range of 0.010 to 0.40 inches. Furthermore, distal end 426 is tilted upwardly such that tangent line T6 forms an angle D1 with respect to lower surface 440 of body 412 in a range of about 20° to 50° and, more preferably, in a range of about 22° to 44°.

Figure 59:
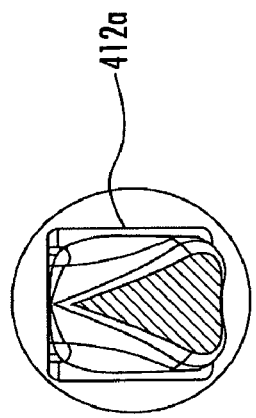
FIG. 59 is a cross-section view taken along line 59-95 of FIG. 55.
Figure 58:
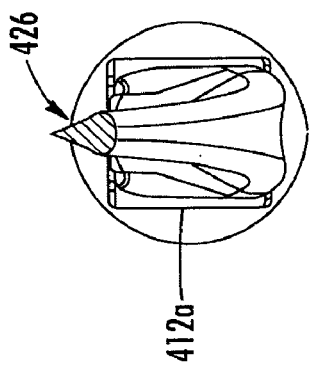
FIG. 58 is a cross-section view taken along line 58-58 of FIG. 55.
Figure 61:
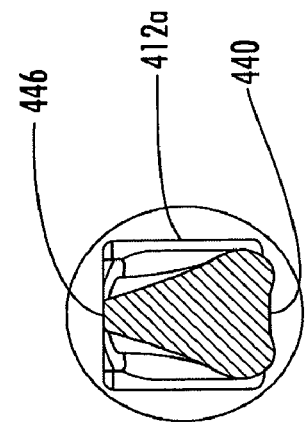
FIG. 61 is a cross-section view taken along line 61-61 of FIG. 55.
Figure 60:
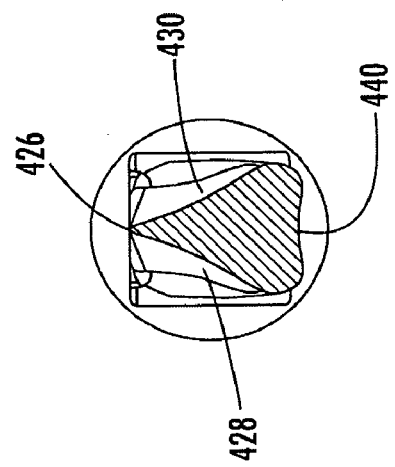
FIG. 60 is a cross-section view taken along line 60-60 of FIG. 55.
Figure 65:
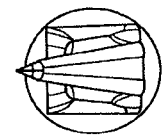
FIG. 65 is a distal end elevation view of the wedge of FIG. 62.
Figure 63:
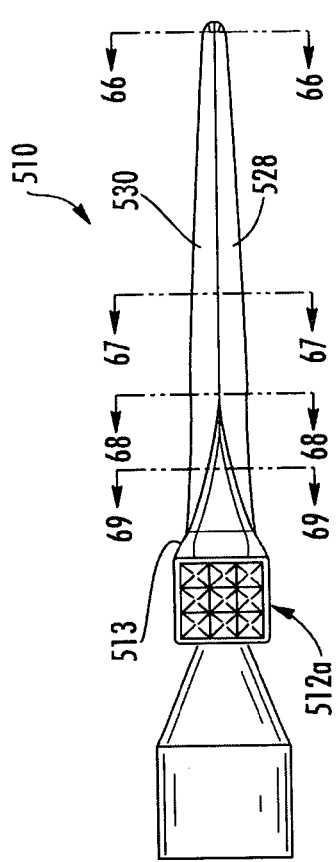
FIG. 63 is a top plan view of the wedge of FIG. 62.
Figure 64:
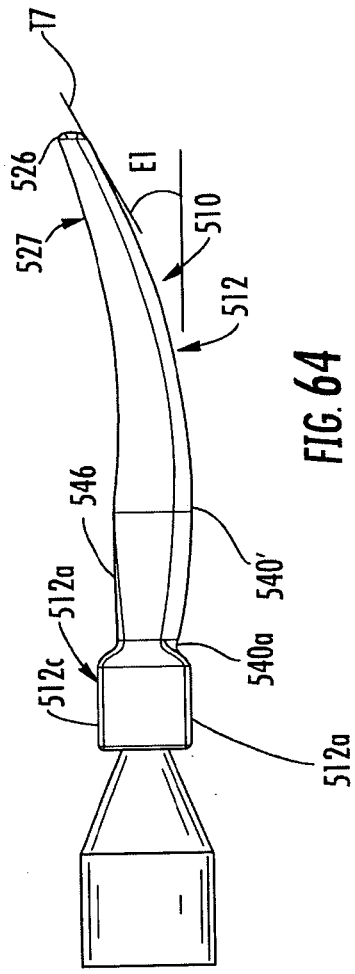
FIG. 64 is a side elevation view of the wedge of FIG. 62.
Figure 62:
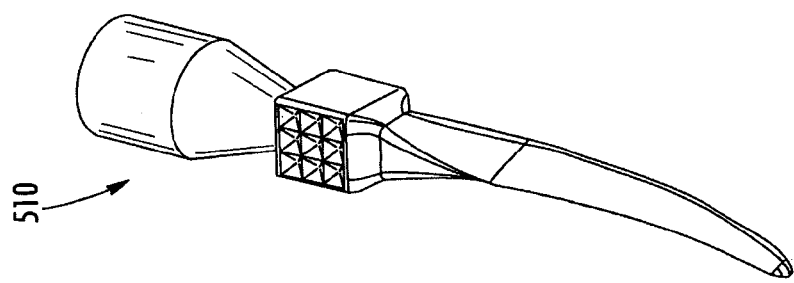
FIG. 62 is a perspective view of the seventh embodiment of the wedge of the present invention.

As best seen in FIG. 55, sides 428 and 430 of elongate body 412 form a reduced cross-section such that upper side 436 has a width dimension that is less than the width dimension of the proximal end portion 412a and a lower side 440 width that also has a smaller width dimension than the width of proximal end portion 412a (FIG. 57). Furthermore, similar to the previous embodiment, the width dimension of upper side 436 is smaller than the width dimension of lower surface 440 at the interface with proximal portion 412a to form a trapezoidal cross-section, which transitions to a triangular cross-section before the medial portion of elongate body 412 so that the medial portion of body 412 has a generally triangular-shaped cross-section. Similarly, corners of lower side 440 are rounded and have radii of curvature in a range of about 0.005 to 0.040 inches and, more preferably, in a range of about 0.008 to 0.028 inches. In addition, as best seen in FIGS. 59–61, lower surface 440 has a reverse curve curvature with a radius of curvature that varies in a range of about 0.050 to 0.120 inches and, more preferably, in a range of about 0.070 to 0.11 inches. As will be understood, wedge 410, therefore, provides a wedge that has a slimmer profile than wedge 310, which may be more suitable for placement between teeth with smaller interproximal spaces.

Referring to FIGS. 62–69, wedge 510 incorporates yet an even further slimmer profile but with a distal end 526 that has an increased upward taper. In addition, elongate body 512 has a tapered interface 513 with proximal end portion 512a to provide an even further reduced cross-section and, hence, forms a slimmer wedge than the previous embodiments. Distal end portion 527 is similarly tapered upwardly such that it extends above proximal portion 512a and, further, above insertion implement 518, for example, in a range of 0.010 to 0.18 inches and, more preferably, in a range of about 0.006 to 0.018 inches. In addition, distal end 526 forms a tangent line T7, which is angled at an angle E1 in a range of about 15° to 35° and, more preferably, in a range of about 20° to 30° with respect to the lower most surface bottom surface 540 of elongate body 512.

Figure 66:
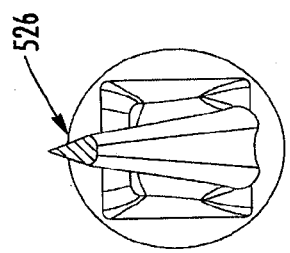
FIG. 66 is a cross-section view taken along line 66-66 of FIG. 63.
Figure 67:
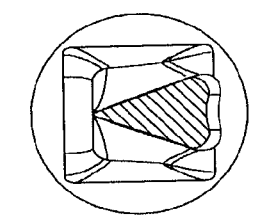
FIG. 67 is a cross-section view taken along line 67-67 of FIG. 63.
Figure 68:
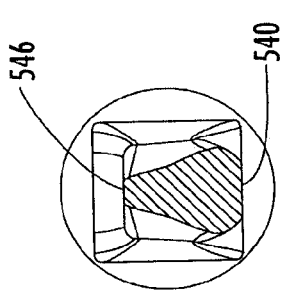
FIG. 68 is a cross-section view taken along line 68-68 if FIG. 63.
Figure 69:
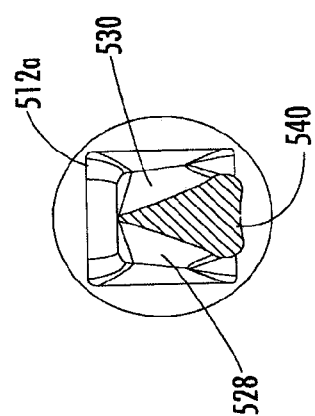
FIG. 69 is a cross-section view taken along line 69-69 of FIG. 63.

Referring to FIGS. 66–69, the cross-section of elongate body 512 similarly transitions from a trapezoidal-shaped cross-section (FIG. 69) to a triangular-shaped cross-section shown in FIGS. 66–68, with its sides 528 and 530 providing a substantially linear taper from interface portion 513 to distal end 526 (as viewed in FIG. 63), where the cross-section of the body increases to form the enlarged rounded or generally spherical shaped distal end, as noted above. In addition, upper side 546 is lowered with respect to the upper surface 512c of proximal portion 512a to provide the slimmer wedge profile. As best seen in FIGS. 64 and 66–68, lower surface 540 of body 512 extends slightly below proximal portion 512a and, further, includes an upwardly turned portion 540a at interface 513 so that proximal end portion 512a may catch on the front side of the tissue, and the tissue will extend up into the recessed portion to provide a limited axial restraint of wedge 510 between the teeth. Similarly, upwardly turned end portion 526 is sufficiently upturned to catch on the backside of the teeth to further limit the axial movement of wedge 510 between the adjacent teeth. It can be appreciated, therefore, that the stepped transition between proximal end portion 512a and the adjacent portion of elongate body 512 provide for increased stability and retention of the wedge when the wedge is inserted between adjacent teeth.

Referring to FIGS. 70–73, wedges 610 and 710 have elongate bodies 612 and 712, respectively, that have single cross-sectional shapes along their lengths, with their cross-sectional dimensions varying along their lengths to create elongate bodies that taper from their proximal ends 620, 720 to their respective distal ends 626 and 726.

As best seen in FIG. 71, elongate body 612 of wedge 610 is formed from an upper side or surface 646, a pair of angled and curved sides 628 and 630, which extend up from a base side or surface 640 to form a generally trapezoidal-shaped cross-section. Sides 628 and 630 are joined with base surface 640 by radiused corners 642 and 644. For examples of suitable radii of curvature reference is made to the previous embodiments. Similarly, distal end 626 is tilted upwardly with respect to the lowermost surface of elongate body 612 to minimize trauma to the surrounding tissue when inserted. Optionally, distal end 626 may be tapered sufficiently to engage the backside of the teeth when inserted into the interproximal space between the adjacent teeth. For suitable angles of tilt and other details not described more fully herein reference is made to the previous embodiments.

As best seen in FIG. 73, elongate body 712 of wedge 710 is formed from a pair of angled and curved sides 728 and 730, which extend upwardly from base side of surface 740 to form a triangular cross-section. Sides 728 and 730 similarly are joined with base surface 740 by radiused corners 742 and 744. For examples of suitable radii of curvature, reference is made to the previous embodiments. Similarly, distal end 726 is tilted upwardly with respect to the lowermost surface of elongate body 712 to minimize trauma to the surrounding tissue when inserted into the interproximal space between adjacent teeth. Optionally, distal end 726 may be tapered sufficiently to engage the backside of the teeth when inserted into the interproximal space between the adjacent teeth. For suitable angles of tilt and other details not mentioned herein reference is made to the previous embodiments.

Though illustrated as being formed from a single or uniform material, it should be understood that wedges 610 and 710 may be formed from more than one material, such as the dual-durometer wedges described previously.

While several forms of the invention have been shown and described, changes and modifications will be apparent to those skilled in the art. For example, one or more corners of the wedge elongate bodies may incorporate textures, such as flocking-ribs, bumps, or the like to increase the retention of the respective wedge between the teeth. In addition, the concepts of all the wedges may be combined or selected features from one wedge may be used in another of the wedges. Further, while several of the wedges have been illustrated with solid cross-sections, it can be appreciated that the wedge body may include hollow portions to provide increased flexibility to the wedge when inserted between the teeth or may be formed from two or more materials. In addition, though dimensions and angles have been provided, these dimensions and angles are exemplary only and are not intended to limit the scope of the claims, which follow.

The invention claimed is:

1. A dental wedge comprising:
an elongate body having a lower surface, a distal end, and a proximal end tapering to said distal end, said distal end defining an insertion end for inserting the interproximal area between adjacent teeth, said elongate body having a first portion starting at said distal end, a second portion ending at said proximal end, and an intermediate portion between said first and second portions, said first portion having a generally triangular-shaped cross-section, said second portion having a generally trapezoidal-shaped cross-section, and said first and second portions angled relative to said intermediate portion wherein said first and second portions are tilted upwardly relative to said lower surface of said intermediate portion; and
wherein said elongate body includes a base side and angled sides, said angles sides depending from said base side and forming said triangular-shaped cross-section and said trapezoidal-shaped cross-section, said angled sides including rounded corners with said base side to reduce trauma to tissue when said wedge is inserted between teeth.

2. The dental wedge according to claim 1, wherein said angled sides include concave portions.

3. A dental wedge comprising:
an elongate body having a distal end, a proximal end tapering to said distal end, an intermediate portion between said distal and proximal ends, and a longitudinal axis, said elongate body further having a lower surface, said distal end defining an insertion end, said elongate body having a core extending along at least a portion of said longitudinal axis, said core comprising a first material having a first hardness, said elongate body having an exterior surface formed from a second material having a second hardness, said exterior surface having a substantially uniform thickness along said longitudinal axis, and said second hardness being less than said first hardness to form a generally soft exterior surface, and said distal and proximal ends being angled with respect to said intermediate portion wherein said distal and proximal ends are tilted upward relative to said lower surface of said intermediate portion to reduce trauma to tissue when said dental wedge is inserted between teeth and wherein said intermediate portion of said elongate body compresses when said wedge is inserted into an interproximal area between adjacent teeth thereby forming enlarged regions on either side of the teeth for abutting the teeth to reduce slippage of said wedge from between the teeth.

4. The dental wedge according to claim 3, wherein said distal end comprises a rounded distal end.

5. The dental wedge according to claim 4, wherein said rounded distal end comprises a generally spherical distal end.

6. The dental wedge according to claim 3, wherein said elongate body has an outer surface, said outer surface being formed from a compressible high friction material.

7. The dental wedge according to claim 6, wherein said high friction material comprises a thermoplastic elastomer.

8. The dental wedge according to claim 3, wherein said elongate body has a first portion starting at said distal end and having a second portion ending at said proximal end, said first portion having a generally triangular shaped cross-section, and said second portion having a generally trapezoidal-shaped cross-section.

9. The dental wedge according to claim 8, wherein said triangular shaped cross-section and said trapezoidal-shaped cross-section define a base side and angled sides, said angled sides depending from said base side, and at least portions of said angled sides comprising concave sides.

10. The dental wedge according to claim 9, wherein said angled sides form rounded corners with said base side to reduce trauma to tissue when said wedge is inserted between teeth.

11. The dental wedge according to claim 3, wherein said first material comprises a material chosen from a plastic material, a metal material, and a wood material.

12. The dental wedge according to claim 3, wherein said second material comprises a thermoplastic elastomer.

13. The dental wedge according to claim 3, wherein said distal end is tilted upwardly at a greater angle than said proximal end.

14. A dental wedge comprising:
an elongate body having a distal end an intermediate portion, and a proximal end tapering to said distal end, said distal end comprising a rounded distal end and defining an insertion end, said elongate body including a base with a base side and a pair of angled tapered sides generally free or protuberances or indentations, said distal end and said proximal end being tilted upwardly with respect to said base wall of said intermediate portion, and said angled tapered sides being joined with said base side and forming rounded corners with said base side wherein said elongate body is free of sharp edges at said base to minimize trauma to tissue when said dental wedge is inserted between teeth.

15. The dental wedge according to claim 14, wherein each of said angled tapered sides includes a concave portion.

16. The dental wedge according to claim 14, wherein said elongate body includes a core and an outer surface softer than said core to reduce the trauma to tissue when said wedge is inserted between teeth.

17. The dental wedge according to claim 16, wherein said outer surface comprises a material having a durometer in a range of about 20 to 90 Shore A.

18. The dental wedge according to claim 17, wherein said outer surface comprises a material having a durometer in a range of about 30 to 60 Shore A.

19. The dental wedge according to claim 14, wherein elongate body includes a first portion having triangular shaped cross-section and a second portion having a generally trapezoidal cross-section, said first portion extending from said distal end, and said second portion extending from said first portion to said proximal end.

20. The dental wedge according to claim 14, wherein said distal end is tilted upwardly relative to said base side at a greater angle than said proximal end for engaging at least one or the tooth when the wedge is inserted Into the interproximal area between the adjacent teeth.

21. The dental wedge according to claim 14, wherein said elongate body has a curved longitudinal axis wherein said distal end is tilted upwardly relative to a center of said proximate end.

22. A dental wedge comprising:
an elongated body having a lower side with a lower surface, a distal end, a proximal end tapering to said distal end, and a longitudinal axis, said distal end comprising a rounded distal end and defining an insertion end for inserting into an interproximal area between adjacent teeth, said distal end tilted upwardly from said longitudinal axis and said lower side, said proximal end tilted upwardly with respect to said lower side, said elongate body including a cross-section with curved sides and at least two rounded corners, said curve sides presenting an increased area of contact with the adjacent teeth and surrounding gum tissue wherein said increased area of contact reduces slippage of said dental wedge and said rounded corners and rounded distal end reduce trauma to the tissue when said dental wedge is inserted in the interproximal area between adjacent teeth.

23. The dental wedge according to claim 22, wherein said elongated body includes an exterior surface comprising a high friction material wherein said high friction material further reduces slippage of said dental wedge from between the adjacent teeth.

24. The dental wedge according to claim 23, wherein said elongate body includes a core and an outer surface having a lower durometer than said core to reduce the trauma to tissue when said wedge is inserted between teeth.

25. The dental wedge according to claim 22, wherein said exterior surface is generally free of protuberances and recesses.

26. The dental wedge according to claim 22, wherein at least a first portion of said elongate body has a triangular-shaped cross-section.

27. The dental wedge according to claim 26, wherein a second portion of said elongate body has a trapezoidal-shaped cross-section.

28. The dental wedge according to claim 22, wherein each of said rounded corners has a radius of in a range of about 0.010 inches to 0.05 inches.

29. The dental wedge according to claim 22, wherein said distal end is tilted upwardly relative to said lower surface wherein said distal end abuts at least one of the teeth when said wedge is inserted into the interproximal area between the teeth to resist pull out of the wedge.

* * * * *

UNITED STATES PATENT AND TRADEMARK OFFICE
CERTIFICATE OF CORRECTION

PATENT NO. : 7,223,101 B2  Page 1 of 1
APPLICATION NO. : 10/608203
DATED : May 29, 2007
INVENTOR(S) : Tom Garrison and Robert Anderson It is certified that error appears in the above-identified patent and that said Letters Patent is hereby corrected as shown below:

Column 5:
Line 20, "95" should be --59--.

Column 9:
Line 48, "farther" should be --further--.

Column 15:
Line 46, Claim 14, "or" should be --of-- in the first occurrence.

Column 16:
Line 10, Claim 20, "or" should be --of--.
Line 10, Claim 20, "tooth" should be --teeth--.
Line 10, Claim 20, "Into" should be --into--.

Signed and Sealed this

Second Day of September, 2008

JON W. DUDAS
*Director of the United States Patent and Trademark Office*